(12) United States Patent
Wahlstrand et al.

(10) Patent No.: US 9,149,628 B2
(45) Date of Patent: *Oct. 6, 2015

(54) NEUROSTIMULATOR FOR TREATING OCCIPITAL NEURALGIA WITH HOUSING SIZED AND CURVED TO CONFORM TO A SUBCUTANEOUS NECK REGION

(71) Applicant: Medtronic, Inc., Minneapolis, MN (US)

(72) Inventors: Carl D. Wahlstrand, North Oaks, MN (US); Robert M. Skime, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,195

(22) Filed: Dec. 20, 2013

(65) Prior Publication Data

US 2014/0107749 A1 Apr. 17, 2014

Related U.S. Application Data

(60) Continuation of application No. 12/480,467, filed on Jun. 8, 2009, now Pat. No. 8,620,437, which is a division of application No. 11/077,603, filed on Mar. 11, 2005, now Pat. No. 7,555,345.

(51) Int. Cl.
```
A61N 1/36        (2006.01)
A61N 1/05        (2006.01)
A61N 1/04        (2006.01)
A61N 1/375       (2006.01)
```

(52) U.S. Cl.
CPC ............ *A61N 1/0504* (2013.01); *A61N 1/0456* (2013.01); *A61N 1/0476* (2013.01); *A61N 1/0492* (2013.01); *A61N 1/0502* (2013.01); *A61N 1/36071* (2013.01); *A61N 1/3756* (2013.01)

(58) Field of Classification Search
CPC .................................................... A61N 1/3756
See application file for complete search history.

(56) References Cited

U.S. PATENT DOCUMENTS

| | | | |
|---|---|---|---|
| 4,254,776 A | 3/1981 | Tanie et al. |
| 4,509,521 A | 4/1985 | Barry |
| 4,627,438 A | 12/1986 | Liss et al. |
| 4,856,526 A | 8/1989 | Liss et al. |
| 5,193,539 A | 3/1993 | Schulman et al. |

(Continued)

FOREIGN PATENT DOCUMENTS

WO   WO 03/033068   4/2003

OTHER PUBLICATIONS

Prosecution History from U.S. Patent No. 7,231,256, from Feb. 15, 2007 through Mar. 1, 2007, 15 pp.

(Continued)

*Primary Examiner* — Kennedy Schaetzle
(74) *Attorney, Agent, or Firm* — Shumaker & Sieffert, P.A.

(57) ABSTRACT

The disclosure describes an implantable neurostimulator device for delivery of neurostimulation to treat head, neck, or facial pain or tension, including pain or tension caused by occipital neuralgia. The device may be a neurostimulation device having a miniaturized housing with a low profile that permits subcutaneous implantation at a stimulation site directly adjacent a neuralgic region at the back of the neck of a patient. For example, the device may be subcutaneously implanted at the back of the neck of a patient to relieve symptoms of occipital neuralgia.

38 Claims, 13 Drawing Sheets

(56) References Cited

U.S. PATENT DOCUMENTS

| | | |
|---|---|---|
| 5,193,540 A | 3/1993 | Schulman et al. |
| 5,215,086 A | 6/1993 | Terry, Jr. et al. |
| 5,447,521 A | 9/1995 | Anderson et al. |
| 5,540,734 A | 7/1996 | Zabara |
| 5,562,718 A | 10/1996 | Palermo |
| 5,578,060 A | 11/1996 | Pohl et al. |
| 5,646,586 A | 7/1997 | Castonguay et al. |
| 5,653,739 A | 8/1997 | Maurer et al. |
| 5,895,414 A | 4/1999 | Sanchez-Zambrano |
| 5,961,542 A | 10/1999 | Agarwala |
| 5,987,352 A | 11/1999 | Klein et al. |
| 6,016,449 A | 1/2000 | Fischell et al. |
| 6,041,259 A | 3/2000 | Agarwala et al. |
| 6,052,624 A | 4/2000 | Mann |
| 6,061,593 A | 5/2000 | Fischell et al. |
| 6,128,538 A | 10/2000 | Fischell et al. |
| 6,134,474 A | 10/2000 | Fischell et al. |
| 6,176,879 B1 | 1/2001 | Reischl et al. |
| 6,269,266 B1 | 7/2001 | Leysieffer |
| 6,301,500 B1 | 10/2001 | Van Herk et al. |
| 6,356,788 B2 | 3/2002 | Boveja |
| 6,360,122 B1 | 3/2002 | Fischell et al. |
| 6,366,814 B1 | 4/2002 | Boveja et al. |
| 6,381,496 B1 | 4/2002 | Meadows et al. |
| 6,445,955 B1 | 9/2002 | Michelson et al. |
| 6,473,653 B1 | 10/2002 | Schallhorn et al. |
| 6,505,075 B1 | 1/2003 | Weiner |
| 6,526,318 B1 | 2/2003 | Ansarinia |
| 6,622,048 B1 | 9/2003 | Mann et al. |
| 6,647,292 B1 | 11/2003 | Bardy et al. |
| 6,647,296 B2 | 11/2003 | Fischell et al. |
| 6,662,051 B1 | 12/2003 | Eraker et al. |
| 6,662,052 B1 | 12/2003 | Sarwal et al. |
| 6,735,475 B1 | 5/2004 | Whitehurst et al. |
| 6,871,099 B1 | 3/2005 | Whitehurst et al. |
| 6,944,503 B2 | 9/2005 | Crowe et al. |
| 7,218,964 B2 | 5/2007 | Hill et al. |
| 7,231,256 B2 | 6/2007 | Wahlstrand et al. |
| 7,299,093 B2 | 11/2007 | Zhu et al. |
| 7,555,345 B2 | 6/2009 | Wahlstrand et al. |
| 7,664,552 B2 | 2/2010 | Wahlstrand et al. |
| 7,676,271 B2 | 3/2010 | Wahlstrand et al. |
| 8,295,936 B2 | 10/2012 | Wahlstrand et al. |
| 8,620,437 B2 | 12/2013 | Wahlstrand et al. |
| 2001/0003799 A1 | 6/2001 | Boveja |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0099412 A1 | 7/2002 | Fischell et al. |
| 2002/0138116 A1 | 9/2002 | Bertolucci |
| 2002/0161403 A1 | 10/2002 | Meadows et al. |
| 2002/0198572 A1 | 12/2002 | Weiner |
| 2003/0004428 A1 | 1/2003 | Pless et al. |
| 2003/0097161 A1 | 5/2003 | Firlik et al. |
| 2003/0109903 A1 | 6/2003 | Berrang et al. |
| 2003/0114905 A1 | 6/2003 | Kuzma |
| 2003/0125786 A1 | 7/2003 | Gliner |
| 2003/0208248 A1 | 11/2003 | Carter et al. |
| 2003/0236557 A1 | 12/2003 | Whitehurst et al. |
| 2004/0002635 A1 | 1/2004 | Hargrove et al. |
| 2004/0054297 A1 | 3/2004 | Wingeier et al. |
| 2004/0172089 A1 | 9/2004 | Whitehurst et al. |
| 2004/0215249 A1 | 10/2004 | Corbucci |
| 2004/0215288 A1 | 10/2004 | Lee et al. |
| 2006/0206162 A1 | 9/2006 | Wahlstrand et al. |
| 2006/0206163 A1 | 9/2006 | Wahlstrand et al. |
| 2007/0162087 A1 | 7/2007 | Wahlstrand et al. |
| 2009/0234420 A1 | 9/2009 | Wahlstrand et al. |
| 2009/0240303 A1 | 9/2009 | Wahlstrand et al. |
| 2010/0049277 A1 | 2/2010 | Wahlstrand et al. |

OTHER PUBLICATIONS

Prosecution History from U.S. Patent No. 7,676,271, from Nov. 20, 2009, 9 pp.

Prosecution History from U.S. Patent No. 7,664,552, from Apr. 8, 2009 through Oct. 13, 2009, 31 pp.

Prosecution History from U.S. Patent No. 7,555,345, from Aug. 31, 2007 through Apr. 15, 2009, 91 pp.

Prosecution History from U.S. Patent No. 8,295,936, from Jun. 1, 2009 through May 7, 2012, 45 pp.

Prosecution History from U.S. Patent No. 8,620,437, from Oct. 16, 2012 through Aug. 22, 2013, 35 pp.

Prosecution History from U.S. Appl. No. 12/611,504, from Jul. 2, 2013 through Jan. 21, 2014, 40 pp.

Written Opinion of International application No. PCT/US2006/003727, mailed Oct. 31, 2006, 6 pp.

NEUROSTIMULATOR FOR TREATING OCCIPITAL NEURALGIA WITH HOUSING SIZED AND CURVED TO CONFORM TO A SUBCUTANEOUS NECK REGION

This application is a continuation of U.S. application Ser. No. 12/480,467, filed Jun. 8, 2009, now U.S. Pat. No. 8,620,437, which is a divisional of U.S. application Ser. No. 11/077,603, filed Mar. 11, 2005, now U.S. Pat. No. 7,555,345, the entire content of each application is incorporated herein by reference.

TECHNICAL FIELD

The invention relates to medical devices, and more particularly, to medical devices for delivery of neurostimulation.

BACKGROUND

Implantable neurostimulator devices are used to deliver therapy to patients to treat a variety of symptoms or conditions such as chronic pain, tremor, Parkinson's disease, epilepsy, incontinence, sexual dysfunction, or gastroparesis. The neurostimulator delivers neurostimulation therapy via one or more leads that include electrodes located proximate to the spinal cord, pelvic nerves, or stomach, or within the brain of a patient. In general, the neurostimulator delivers neurostimulation therapy in the form of electrical pulses.

Depending on the application for which they are implanted in a patient, neurostimulators may include a variety of electrical and/or mechanical components. Typically, a neurostimulator includes a rigid housing that houses all of its components, which are generally fragile, to protect the components from forces to which they would otherwise be exposed when implanted within the human body. The size and shape of a neurostimulator housing is dependent on the sizes and shapes of the components of the neurostimulator.

A neurostimulator is typically implanted within the abdomen, upper pectoral region, or subclavicular region of a patient. Leads or catheters are used to deliver therapy or monitor a physiological parameter at a remote location of the body. The leads or catheters extend from the neurostimulator housing for placement at a target site.

Implantation and positioning of leads and catheters can be difficult and time-consuming from the perspective of a surgeon, particularly where the neurostimulator is located a significant distance from the treatment or monitoring site. The increased surgical time, increased surgical trauma, and increased amount of implanted material associated with the use of leads and catheters can increase the risk to the patient of complications associated with the implantation of a neurostimulator.

In addition, selection of an efficacious target site for deployment of a lead or catheter is difficult. Some leads include an array of electrodes that can be selectively activated to target different nerve sites or create different energy fields. Once a lead is in place, however, repositioning of the lead is generally undesirable. In particular, the patient ordinarily must undergo an additional surgical procedure with associated risks. Accordingly, selection of a nerve site appropriate for therapeutic efficacy continues to be a concern.

SUMMARY

In general, the invention is directed to neurostimulators and methods for delivery of neurostimulation to treat head, neck, or facial pain or tension, including pain or tension caused by occipital neuralgia. The neurostimulation may be delivered to a stimulation site that generally resides within the upper cervical region of the spine, e.g., C1-C4, and may target occipital nerves and branches in that region. The neurostimulator may be a neurostimulation device having a miniaturized housing with a low profile that permits subcutaneous implantation at a stimulation site directly adjacent a neuralgic region at the back of the neck of a patient. For example, the neurostimulator may be subcutaneously implanted at the back of the neck of a patient to relieve symptoms of occipital neuralgia.

The housing may also have a degree of curvature to at least partially conform to a radius of the stimulation site. The housing may be pre-formed with a degree of curvature so that the housing at least partially conforms to a surface at a stimulation site, such as the back of the neck of a patient. In other cases, the housing may be bent or curved to a degree of curvature appropriate for a specific stimulation site. As an example, the housing may include a bellows-like joint to allow the first and second portions of the housing to move relative to another.

The neurostimulator may include an array of electrodes that permits selection of electrode combinations to target specific stimulation sites. The electrodes may be formed on a surface of the neurostimulator housing, e.g., as pad electrodes or ring electrodes. In some embodiments, the electrodes may be arranged in a two-dimensional array across a surface of the neurostimulator. In other embodiments, an array of electrodes may be coupled to the device housing with a lead.

In one embodiment, the invention is directed to a neurostimulator comprising a pulse generator that generates neurostimulation pulses, a battery within the housing that powers the pulse generator, a set of electrodes, coupled to the pulse generator, that delivers the neurostimulation pulses, and a device housing that houses the pulse generator and the battery, wherein the device housing is shaped to at least partially conform to a subcutaneous region within a back of a neck of a patient.

In another embodiment, the invention is directed to a method comprising implanting a neurostimulator device at a subcutaneous location within a back of a neck of a patient, and applying neurostimulation energy from the neurostimulator device to alleviate symptoms of occipital neuralgia.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
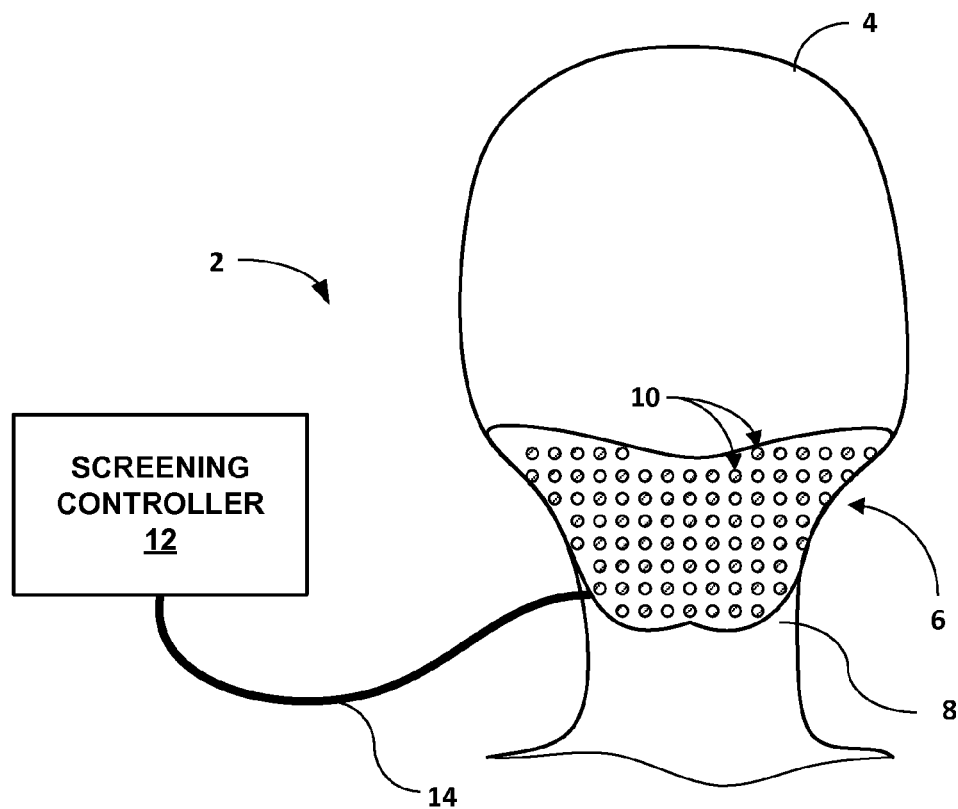
FIG. 1 is a schematic diagram illustrating a transcutaneous stimulation screening device.

FIG. 1 is a schematic diagram illustrating a transcutaneous neurostimulation screening system 2. The transcutaneous stimulation screening system 2 may be used to non-invasively select a stimulation region to treat head ache, neck ache, or facial pain or tension, including pain or tension caused by occipital neuralgia. The neurostimulation may generally be directed to the upper cervical region of the spine, e.g., C1-C4, and may target occipital nerves and peripheral nerve branches in that region. Also, in some cases, system 2 may stimulate muscle tissue instead or, or in addition to, nerves in the upper cervical region.

System 2 may be applied to treat symptoms of occipital neuralgia. Occipital neuralgia is a chronic pain disorder caused by irritation or injury to the occipital nerve, which is located at the back of the neck. Occipital neuralgia may cause pain, often described as throbbing and migraine-like, originating at the nape of the neck and spreading up and around the forehead and scalp. Occipital neuralgia can result from physical stress, trauma, or repeated contraction of the muscles of the neck. Although application of the invention to occipital neuralgia will be described herein for purposes of example, the invention may be applied to alleviate pain or tension caused by other neurological disorders in the upper cervical region.

The transcutaneous stimulation screening system 2 illustrated in FIG. 1 is used to select a stimulation region adjacent a neuralgic region of a patient 4. Upon selection of the stimulation region, a neurostimulator (not shown in FIG. 1) may be subcutaneously implanted in the stimulation region on a chronic basis to substantially alleviate the pain experienced by the patient. As will be described, the neurostimulator may comprise a neurostimulator device with a miniaturized form factor and a low profile to allow implantation at the stimulation site. For occipital neuralgia, the neurostimulator may be subcutaneously implanted at a stimulation site generally located in the back of the neck of the patient.

Alternatively, additional screening can be performed to narrow the stimulation region to a preferred stimulation site. For example, an additional stimulation screening system, in the form of a percutaneous needle electrode array, may be applied to patient 4 to more precisely identify a stimulation site prior to chronic implantation of a neurostimulator. As a further alternative, application of the transcutaneous stimulation screening system may be followed by the percutaneous needle electrode array, and then by a temporary neurostimulator implanted at the stimulation site, prior to implantation of a chronic neurostimulator. The temporary neurostimulator may provide a trial screening period to evaluate the efficacy of neurostimulation in the relief of symptoms of occipital neuralgia. These alternatives will be described in further detail below.

With further reference to FIG. 1, transcutaneous stimulation screening system 2 includes an electrode array patch 6 and a screening controller 12. Electrode array patch 6 may be applied to an epidermal region 8 of a patient's head, adjacent to a neuralgic region. A caregiver, such as a physician or clinician, may perform imaging of the head of the patient 4, e.g., using magnetic resonance imaging (MRI), to identify epidermal region 8. In the example of FIG. 1, electrode array patch 6 is applied to epidermal region 8 on the back of the neck of the patient 4, which is adjacent the occipital nerve of the patient.

Electrode array patch 6 comprises an array of electrodes 10 formed on a carrier. Electrode array patch 6 may conform to epidermal region 8. In some embodiments, electrode array patch 6 may comprise a rigid material pre-formed to the contour of epidermal region 8, e.g., by casting or molding. In other cases, electrode array patch 6 may comprise a flexible material that is formable to the contour of epidermal region 8, e.g., much like flex circuitry. Exemplary materials for the carrier include silicone, polyurethane, polyester, and polyimide.

In some embodiments, electrodes 10 may be formed as electrically conductive pads that are deposited, printed or etched onto the dielectric carrier, along with conductive traces to couple the electrodes to a cable 14. Cable 14 couples electrodes 10 to screening controller 12. In some embodiments, electrodes 10 may have peaked, spherical, or contoured surfaces designed to enhance coupling pressure and increase contact area with the patient's skin. Cable 14 may include a separate electrical conductor for each electrode 10 so that the electrodes can be independently energized to deliver stimulation energy. Electrode array patch 6 may be a single layer or multi-layer construction, depending on the density of electrodes 10 and associated conductive traces.

Electrode array patch 6 may have a length of approximately 15 to 20 cm, and a height of approximately 10 to 15 cm. In an exemplary embodiment, electrode array patch 6 includes approximately 10 to 150, and more preferably 30 to 100, electrodes 10. Electrodes 10 may be formed as circular, square or rectangular, electrically conductive pads. Each electrode 10 may have a surface area in a range of approximately 0.15 to 1.0 cm$^2$. Electrodes 10 may be arranged in a linear array or two-dimensional array of columns and rows, or in a recurring diagonal pattern. Conductive traces may access electrodes 10 directly on the outer surface of the carrier, or from another layer below the outer surface using conductive vias. In some embodiments, cable 14 may be removably coupled to a connector carried by electrode array patch 6.

Figure 2:
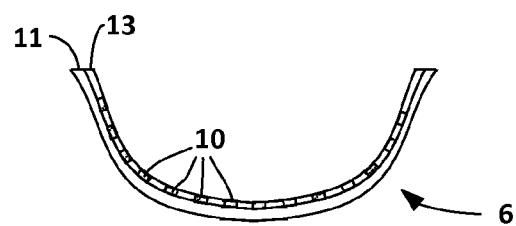
FIG. 2 is a side view of an electrode array patch shown in FIG. 1.

Electrode array patch 6 may be adhesively attached to the neck of the patient 4. In this case, electrode array patch 6 may include an integrated adhesive layer. FIG. 2 is a side view of electrode array patch 6 shown in FIG. 1. In the example of FIG. 2, electrode array patch 6 includes a carrier layer 11, an array of electrodes 10 formed on the carrier layer, and an adhesive layer 13 on a side of the carrier layer adjacent the electrodes. The adhesive layer 13 may be formulated to incorporate an electrically conductive gel for enhanced electrical coupling between electrodes 10 and the patient's neck. An appropriate release layer (not shown in FIG. 2) may be applied to the adhesive layer upon manufacture to permit storage of the electrode array patch.

As an alternative, electrode array patch may be held in place by straps, sutures, adhesive tape, surgical adhesives, or the like. As a further alternative, electrode array patch 6 may form part of a head rest that supports the head of patient 4. In this manner, gravity forces the patient's head into contact with electrodes 10 on electrode array patch 6. Filling the carrier layer or an adjacent layer with a gel-like material may further support conformity of electrode array patch 6 to the head of patient 4.

Electrode array patch 6 positions electrodes 10 adjacent epidermal region 8 of patient 4 to apply transcutaneous electrical neurostimulation, sometimes referred to as "TENS," to the neuralgic region of patient 4. In other embodiments, the screening device may utilize another non-invasive way to introduce energy to a patient instead of TENS. Examples include sonic diathermy, radio frequency (RF) diathermy, standard heating, and standard cooling. Patient response to application of stimulation in any of these diverse forms may be helpful in identifying a stimulation site for neurostimulation.

Each of electrodes 10 may be controlled to deliver stimulation independently or simultaneously with other electrodes as a group, e.g., in a unipolar or bipolar configuration. Electrodes 10 may be arranged in a grid pattern, as illustrated in FIG. 1. In other embodiments, electrodes 10 may be arranged in other patterns associated with a specific neuralgic region. Electrodes 10 on electrode array patch 6 are positioned adjacent epidermal region 8 of patient 4.

Screening controller 12 permits a caregiver to selectively activate different electrodes 10, or combinations of electrodes, and thereby move an electrical stimulation pattern across electrode array patch 6. In this manner, the electrical stimulation pattern can be adjusted to access different potential stimulation regions and evaluate the efficacy of neurostimulation at those sites. In some embodiments, one of the electrodes 10 may serve as a reference electrode for individual electrodes selected by screening controller 12, providing a unipolar arrangement. The reference electrode may be placed on a skin surface of the patient or included in the array of electrodes 10 on the electrode array patch 6. The reference electrode is preferably at least two centimeters away from the other electrodes 10 to produce a far field effect for unipolar arrangements. Alternatively, screening controller 12 may select bipolar pairs of electrodes.

A caregiver operates screening controller 12 to select one or more stimulation regions within epidermal region 8 that substantially alleviate the pain experienced by patient 4. Screening controller 12 may include a joystick to move the stimulation up, down, left, or right across electrode array patch 6, as will be described with reference to FIG. 3. In other embodiments, controller 12 may comprise arrow keys or the like to manually position the stimulation. In some cases, screening controller 12 may comprise a computing device that automatically moves the stimulation across electrode array patch 6.

As the electrical stimulation pattern moves across different electrode combinations within electrode array patch 6, the caregiver collects feedback from patient 4 regarding the effects of the stimulation in relieving the patient's pain symptoms. The caregiver may record the feedback within screening controller 12 using an input device such as a keyboard or keypad, or manually record the feedback. In either case, the feedback is associated with the particular electrode combination selected at the time the feedback is elicited.

The feedback may comprise an assessment of the amount of pain experienced by the patient during the stimulation. The feedback may be provided on any of a variety of efficacy rating scales, including numeric and qualitative pain scales, or combinations of such scales. One example of a pain rating scale is the visual analog scale. Efficacy feedback also may include feedback concerning undesirable side effects such as pain due to high current density, unwanted parasthesia reference to other parts of the body, or dizziness. In some cases, the patient may be permitted to record the feedback directly in screening controller 12, e.g., via a keyboard. For example, patient 4 may provide the feedback to screening controller 12 directly via an input device such as a button or a keypad. In other embodiments, the caregiver may enter the feedback from the patient to screening controller 12.

In operation, screening controller 12 stimulates one or more electrodes 10 corresponding to a first stimulation region within epidermal region 8 and receives feedback from the patient regarding the stimulation region. Screening controller 12 then drives one or more electrodes 10 to deliver stimulation energy within a second stimulation region within epidermal region 8 and receives feedback from the patient regarding the second stimulation site. The second stimulation region may be located adjacent the first stimulation region within epidermal region 8. In some cases, the second stimulation region may overlap the first stimulation region.

The electrode selection process may be automated, in some embodiments, to systematically step through adjacent electrode combinations situated across electrode array patch 6. The selection process may be designed to focus on electrode combinations adjacent a given region once efficacious results are achieved using other electrode combinations in that region. For example, screening controller 12 may automatically select electrode combinations using electrodes 10 that "orbit" about an electrode or electrode combination found to provide good results, before moving on to other regions of electrode array patch 6.

Alternatively, the caregiver may manually operate screening controller 12 to move the stimulation pattern in response to the feedback from patient 4. For example, when the feedback regarding a first stimulation region indicates at least partial pain alleviation, the caregiver may manipulate screening controller 12 to define several stimulation regions that overlap the first stimulation region. However, when the feedback regarding the second stimulation region indicates no or insufficient pain alleviation, the caregiver may manipulate screening controller 12 to define the next stimulation regions adjacent the first stimulation region.

As mentioned above, screening controller 12 may be configured to record efficacy results based on feedback from the patient. Alternatively, in other embodiments, screening controller 12 may simply include an input media, such as a key or button, to permit the caregiver to mark electrode combinations, and stimulation regions, found to provide especially good alleviation of the patient's symptoms. In either cases, screening controller 12 stores the marked stimulation regions, and optionally the feedback associated with such sites.

Once the transcutaneous stimulation screening is complete, the caregiver selects a stimulation region from the marked stimulation regions based on the feedback and an implantation risk identified for each of the marked stimulation regions. The transcutaneous stimulation screening may be complete when the electrical stimulation pattern has moved across the entire electrode array patch 6, or the caregiver has otherwise terminated the screening. In some embodiments, screening controller 12 may automatically select a stimulation region for recommendation to the caregiver, e.g., based on relative feedback regarding efficacy of the various stimulation regions.

Figure 3:
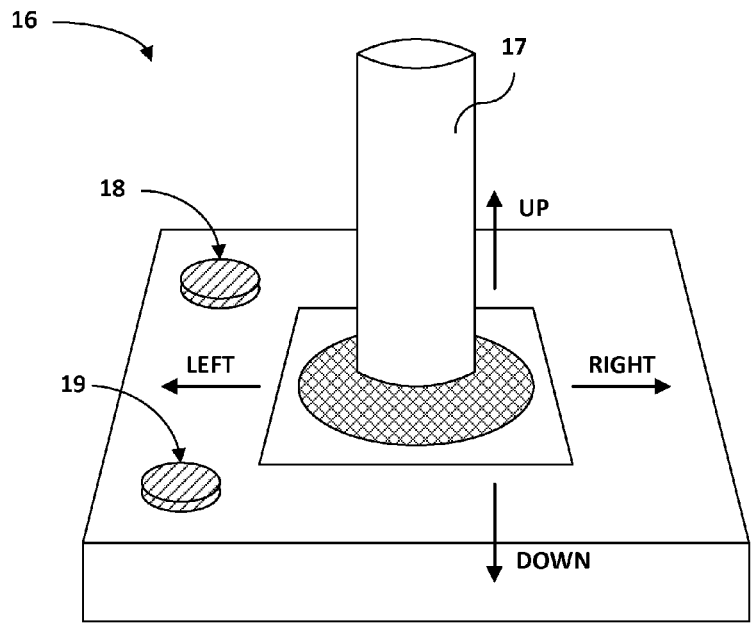
FIG. 3 is a schematic diagram illustrating one example of a controller for use with the screening device from FIG. 1.

FIG. 3 is a schematic diagram illustrating one example of an input device 16 that may form part of screening controller 12 of FIG. 1. As shown in FIG. 3, input device 16 may take the form of a joystick with an actuator stick 17 to select electrode combinations and an input button 18 to activate delivery of transcutaneous neurostimulation. Input device 16 is used to move electrical stimulation across electrode array patch 6 by selection of different combinations of electrodes 10. A first depression of button 18 may be used to trigger delivery of stimulation energy, while a second depression of button 18 terminates delivery of stimulation energy. In addition, a second button 19 can be provided to mark electrode combinations within epidermal region 8 that appear to support efficacy based on feedback from the patient 4. The marked electrode combinations may be recorded by screening controller 12 in response to depression of button 19.

In operation, screening controller 12 drives one or more electrodes 10 that correspond to a first stimulation region. The caregiver then manipulates input device 16 to move the stimulation up, down, left, or right across electrode array patch 6 to one or more electrodes 10 that correspond to a second stimulation region. In some cases, the stimulation may be moved diagonally across electrode array patch 6. The position of the stimulation pattern may be presented graphically on a display device, or by textual information on a display device such as numbers or letters corresponding to electrode combinations.

The caregiver may use input device 16 to move the stimulation in response to feedback from patient 4. For example, when the feedback regarding the first stimulation region indicates at least partial pain alleviation, the physician or clinician may manipulate input device 16 to manually position the second stimulation region in a position overlapping the first stimulation region. Again, positioning may be confirmed by a display device that presents selected electrode combinations, location information, or both. However, when the feedback regarding the first stimulation region indicates no pain alleviation, the caregiver may manipulate input device 16 to manually position the second stimulation at a site adjacent the first stimulation region. Alternatively, as mentioned above, screening controller 12 may be configured to automatically select electrode combinations. Screening controller 12 may permit the caregiver to select either a manual selection mode using input device 16 or an automatic selection mode.

Also, as mentioned above, the caregiver may depress button 19 to mark a stimulation region when the feedback regarding the stimulation region indicates effective pain alleviation. In other embodiments, input device 16 may include additional buttons or a keypad for patient 4, the caregiver, or both to input feedback to controller 12. Controller 12 may store the marked stimulation regions and the corresponding feedback. Once the transcutaneous stimulation screening is complete, the physician or the clinician may select a stimulation region from the marked stimulation regions based on the feedback. In some embodiments, screening controller 12 may select the stimulation region from the marked stimulation regions.

Figure 4:
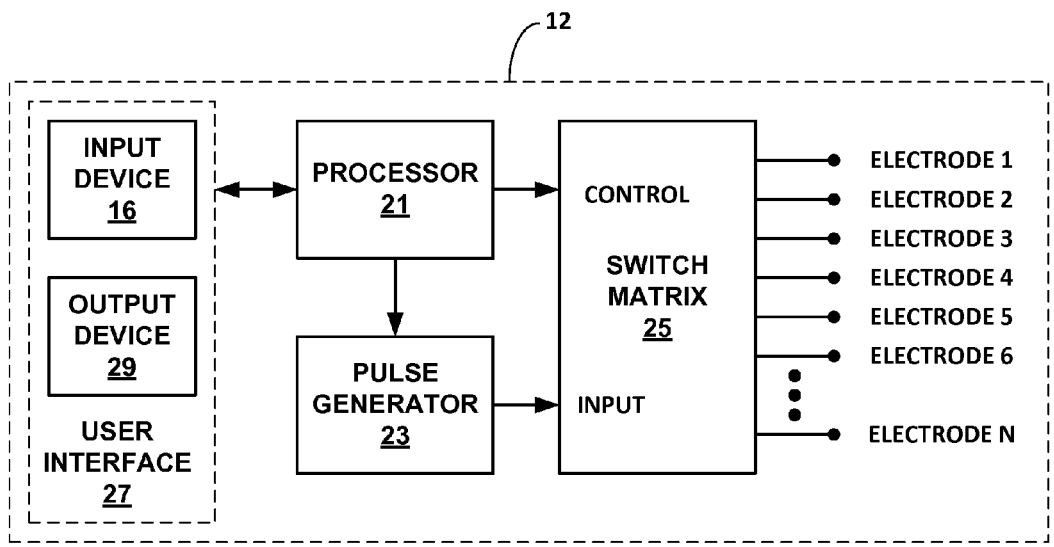
FIG. 4 is a block diagram illustrating the screening controller of FIG. 1 in greater detail.

FIG. 4 is a block diagram illustrating screening controller 12 of FIG. 1 in greater detail. As shown in FIG. 4, screening controller 12 includes a processor 21, a pulse generator 23, switch matrix 25, and a user interface 27. Processor 21 controls pulse generator 23 and switch matrix 25 in response to input from input device 16. In particular, processor 21 activates pulse generator 23 to generate neurostimulation pulses for application across a set of two or more electrodes. Processor 21 may specify parameters such as amplitude, frequency, pulse width and duration for the neurostimulation pulses based on a prestored neurostimulation program, or adjust such parameters in response to input from the caregiver.

As an example, for transcutaneous stimulation to identify a stimulation region, processor 21 may control pulse generator 23 to generate a stimulation waveform having an amplitude of approximately 10 to 100 milliamps, a frequency of approximately 10 to 500 Hz, and more preferably 20 to 200 Hz, a pulse width of approximately 20 to 800 microseconds, and more preferably 80 to 120 microseconds, and a duration of approximately a few seconds to several minutes. The stimulation pulse for transcutaneous stimulation may have a substantially square or spiked waveform. A stimulation waveform having the above parameters should be effective in evaluating efficacy of different stimulation regions. However, screening controller 12 may permit the caregiver to make further adjustments to the stimulation waveform, if desired.

Processor 21 also controls switch matrix 25 to couple selected electrodes 10 to pulse generator 23. As an example, switch matrix 25 may be an array of solid state switches that can be controlled by a codeword generated by processor 21 to couple selected electrodes to pulse generator 23. As the caregiver manipulates input device 16 to activate stimulation and move to different electrode combinations, processor 21 controls pulse generator 23 and switch matrix 25 in a corresponding manner.

User interface 27 includes input device 16 and an output device 29. Input device 16 may include a joystick device, as in FIG. 3, as well as other input media to permit a caregiver or patient to enter information including stimulation commands, efficacy feedback, and the like. Output device 29 may include a display device to present operational and status information during the course of a screening session, and to indicate the position of a particular electrode combination under evaluation. In particular, output device 29 may track the movement of the applied stimulation pattern as a function of joystick movement.

Figure 5:
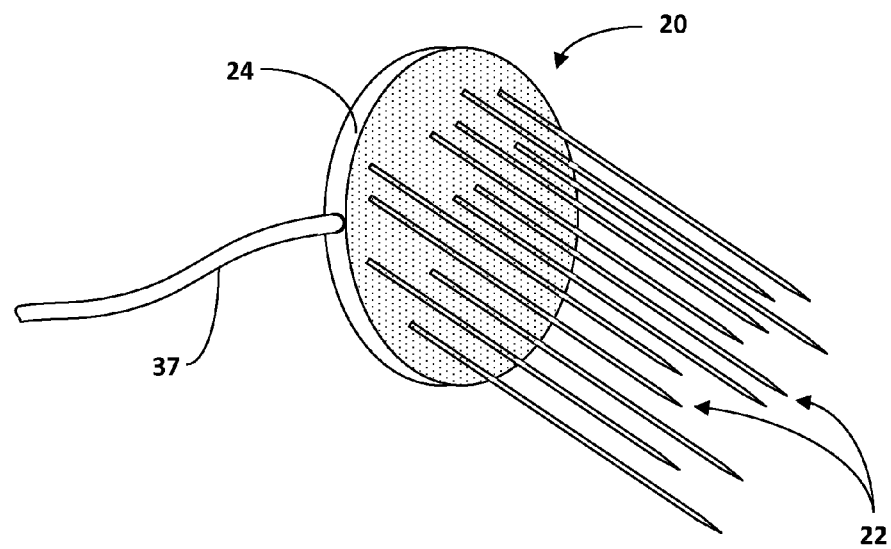
FIG. 5 is a schematic diagram illustrating an example of a micro-electrode screening device.

FIG. 5 is a schematic diagram illustrating an example of a percutaneous micro-electrode needle array screening device 20. Upon selection of an efficacious stimulation region using transcutaneous stimulation screening system 2 (FIG. 1), additional screening techniques can be applied to identify a stimulation site within the selected stimulation region with greater precision. As an example, percutaneous micro-electrode needle array screening device 20 is placed over the stimulation region identified by transcutaneous screening, and then forced into the tissue at the stimulation region such that an array of needle electrodes 22 penetrates the skin and protrudes into the tissue in the epidermal region.

As shown in FIG. 5, device 20 may include a disc-like base 24 supporting the array of needle electrodes 22. A conductor network within base 24 provides multiple, independent electrical conductors. Each conductor is coupled to one of needle electrodes 22 and extends away from base 24 within cable 37. Cable 37 may be connected to screening controller 12 of FIGS. 1, 3 and 4 to couple the individual needle electrodes 22 to switch array 25 and pulse generator 23. In this manner, the needle electrodes 22 receive stimulation energy for percutaneous application to stimulation sites within the stimulation region in the neck of patient 4.

The micro-electrode needle array screening device 20 further localizes the stimulation region selected by the transcutaneous stimulation screening device 2 (FIG. 1) to select a more specific stimulation site at which to chronically implant a neurostimulator for treatment of the neuralgic region of patient 4. If the chronic neurostimulator has an array of electrodes, the localized stimulation site also may permit a caregiver to select an initial combination of electrodes that are positioned to target the stimulation site. Needle electrodes 22 are sized and constructed to permit a caregiver to insert the needles into epidermal region 8. As an example, each needle electrode 22 may have a sharp pointed distal tip, an outer diameter of approximately 250 to 1000 microns, and a length of approximately 5 to 30 mm. Disc-like base 24 may have a diameter of approximately 1 to 5 cm, and a surface area of approximately 70 to 2000 $mm^2$. However, disc-like base 24 need not be circular. Needle electrodes 22 may be distributed across the entire surface of disc-like base 24.

Needle electrodes 22 are constructed from a biocompatible, electrically conductive metal, such as MP (nickel-cobalt) alloy, platinum, stainless steel, or tungsten. However, each needle electrode 22 may be insulated by an outer sheath that extends along substantially the entire length of the needle electrode, leaving a distal tip exposed for delivery of stimulation energy. In this manner, the depth at which the stimulation energy is actually delivered can be controlled by selecting different needle lengths or different outer sheath lengths.

Screening controller 12 is used to move the electrical stimulation across micro-electrode needle array 20. In particular, screening controller 12 selects combinations of two or more electrode needles for delivery of neurostimulation energy. The location of each stimulation site may be presented graphically or textually as the screening process progresses. The parameters for percutaneous delivery of neurostimulation energy may be different than for transcutaneous delivery. For example, the neurostimulation waveform generated by pulse generator 23 for percutaneous stimulation may have an amplitude of approximately 1 to 40 milliamps, and more preferably 6 to 10 milliamps, a frequency of approximately 10 to 500 Hz, and more preferably 20 to 200 Hz, a pulse width of approximately 20 to 800 microseconds, and more preferably 80 to 120 microseconds, and a duration of approximately a few seconds to several minutes. The stimulation pulse for transcutaneous stimulation may have a substantially square or spiked waveform.

As in the case of transcutaneous screening stimulation, the caregiver operates screening controller 12 to localize the selected stimulation region based on the efficacy of the percutaneous stimulation. For example, the caregiver may adjust an input device 16 (FIG. 3) to manually position the stimulation at a selected stimulation site within the stimulation region. Alternatively, screening controller 12 may select different unipolar or bipolar electrode combinations on an automated basis. As the electrical stimulation moves across micro-electrode needle array 20, the caregiver or screening controller 12 receives feedback from patient 4 regarding the efficacy of the stimulation in relieving pain symptoms.

In operation, the percutaneous micro-electrode needle array screening device 20 is used to apply neurostimulation energy to a first stimulation site within epidermal region 8 of patient 4. Screening controller 12 applies stimulation energy via one or more electrodes corresponding to several stimulation sites at the first stimulation site. Screening controller 12 then receives feedback from the patient 4 or the caregiver regarding the efficacy of neurostimulation energy delivered via the selected stimulation site. This process continues until all electrode combinations have been evaluated, or the caregiver terminates the process. Once the stimulation screening is complete, the caregiver may select the best stimulation site based on the feedback and the identified implantation risk for the specific stimulation site. In some embodiments, controller 12 may automatically select the stimulation site, e.g., based on an efficacy rating, and provide a recommendation to the caregiver.

Figure 6:
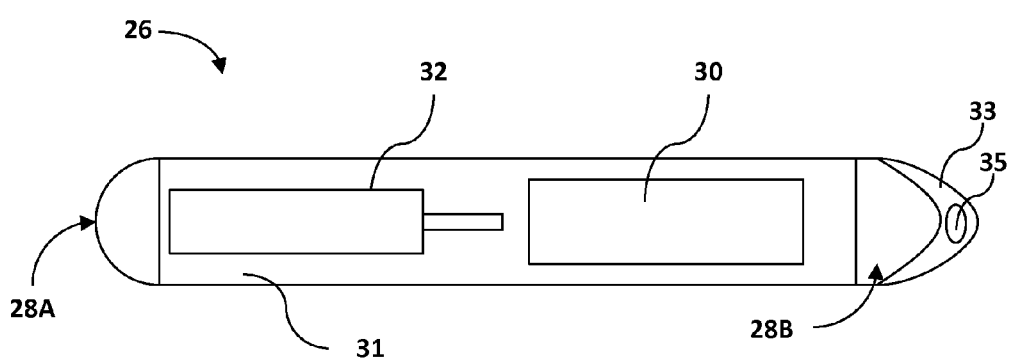
FIG. 6 is a schematic diagram illustrating a temporary implantable screening device.

FIG. 6 is a schematic diagram illustrating a temporary subcutaneous screening device 26. Temporary subcutaneous implantable screening device 26 is subcutaneously implanted in patient 4 at a stimulation site selected by either the transcutaneous stimulation screening device from FIG. 1 or the percutaneous micro-electrode screening device from FIG. 5. Temporary subcutaneous screening device 26 provides temporary electrical stimulation to the neuralgic region of patient 4 to further evaluate the efficacy of the selected stimulation site.

As shown in FIG. 6, temporary subcutaneous implantable screening device 26 includes a housing 31 that carries electrodes 28A-28B (collectively "electrodes 28"), control circuitry 30, and a battery 32. For ease of illustration, electrical conductors coupling electrodes 28, circuitry 30, and battery 32, are not shown in FIG. 6. Housing 31 conforms to a miniaturized form factor that allows subcutaneous implantation of temporary implantable screening device 26 at the stimulation site in the back of the neck of patient 4 adjacent the occipital nerve. Housing 31 may have a potted casing that encapsulates the components.

Circuitry 30 couples to electrodes 28 and battery 32. Battery 32 may be a lithium ion battery. Battery 32 may comprise a pin cell battery or a flat button cell battery. Circuitry 30 includes a pulse generator to generate a neurostimulation waveform for application via electrodes 28A, 28B. Battery 32 provides power to circuitry 30 to generated stimulation energy for electrodes 28 on a temporary basis. Electrodes 28 may be formed on housing 31 as end-cap electrodes or ring electrodes. Battery 32 may have a lifetime of at least one day. In the case of a pin cell, battery 32 preferably has a compression fit feedthrough pin, such as a riveted or crimped feedthrough, and an aluminum case to permit a thin profile. With temporary subcutaneous stimulation device 26, patient 4 can determine whether the selected stimulation site allows substantial pain alleviation before chronic implantation of a neurostimulator.

Temporary subcutaneous screening device 26 also includes a removal loop 33 partially encapsulated in housing 31. Removal loop 33 defines a hole 35 that allows easy explantation of subcutaneous screening device 26 from the selected stimulation site using a hook that extends into hole 35. Accordingly, the caregiver may use a tool with a hook sized to engage with removal loop 33 to pull subcutaneous screening device 26 out of patient 4 when battery 32 runs out of power.

For purposes of temporary screening, circuitry 30 need not be adjustable nor include telemetry electronics. Instead, circuitry 30 may be configured to generate a fixed neurostimulation waveform. For subcutaneous application, the fixed neurostimulation waveform may have a fixed amplitude of approximately 1 to 40 milliamps, and more preferably 6 to 10 milliamps, a fixed frequency of approximately 10 to 800 Hz, and preferably 40 to 60 Hz, a fixed pulse width of approximately 20 to 800 microseconds, and more preferably 80 to 120 microseconds, and a fixed duty cycle in a range of approximately 15 to 25 percent, i.e., "on" for 15 to 25 percent of the time, and more preferably 20 percent of the time.

Subcutaneous screening device 26 may be sized for implantation under a flap of skin in the back of the neck of patient 4. In particular, subcutaneous screening device 26 may have a cylindrical capsule-like shape or generally flat rectangular shape. For a generally flat rectangular shape, device 26 may have a length of approximately 30 to 50 mm, a width of approximately 10 to 20 mm, and a thickness of approximately 3 to 6 mm. For a capsule shape, device 26 may have a length of approximately 30 to 50 mm, and a diameter of approximately 3 to 6 cm. As shown in FIG. 6, subcutaneous screening device 26 may have generally atraumatic rounded ends to promote subcutaneous implantation without substantial discomfort to patient 4. In some embodiments, instead of implantation under a flap of skin, subcutaneous screening device 26 may be introduced via a percutaneous injection needle. As a further alternative, instead of a capsule-like housing, subcutaneous screening device 26 may have a flat or angled housing as described below with reference to the chronically implantable neurostimulator of FIGS. 7-18.

Figure 7:
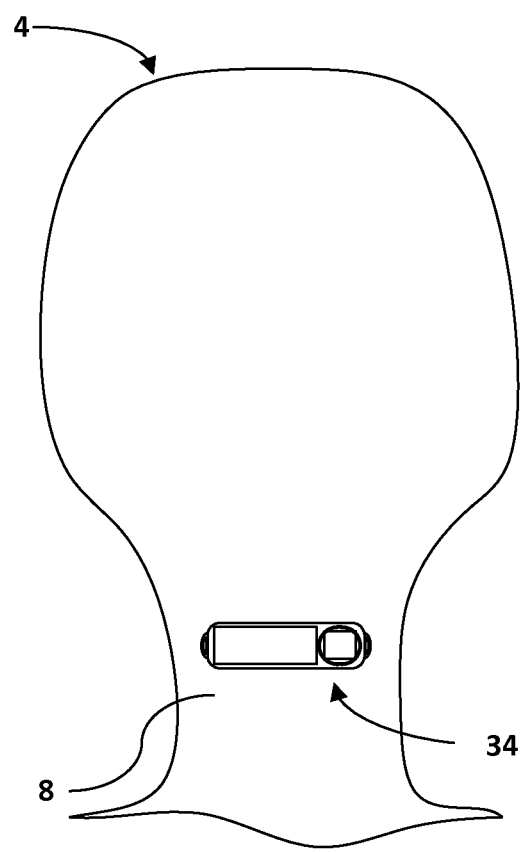
FIG. 7 is a schematic diagram illustrating an example chronic neurostimulator subcutaneously implanted in an occipital nerve region at the back of a neck of a patient.

FIG. 7 is a schematic diagram illustrating an example neurostimulator 34 for chronic subcutaneous implantation in an occipital nerve region at the back of a neck of a patient 4. Once a viable stimulation site is selected based on transcutaneous trial stimulation, percutaneous trial stimulation, and temporary subcutaneous trial stimulation, a neurostimulator 34 can be chronically implanted to provide on-site treatment of neuralgia experienced by patient 4. Neurostimulator 34 may be implanted at a stimulation site tested by temporary subcutaneous screening device 26 from FIG. 6. The caregiver may elect to subcutaneously implant neurostimulator 34 at the stimulation site when the temporary implantable screening device is found to substantially alleviates pain symptoms experienced by patient 4. In addition, in the event the neurostimulator 34 has an array of electrodes, the caregiver may program the neurostimulator to deliver stimulation via a selected combination of electrodes that are best positioned to target the stimulation site.

Neurostimulator 34 has a miniaturized form factor and a low profile that permits subcutaneous implantation at the selected stimulation site directly adjacent the neuralgic region of patient 4. For example, neurostimulator 34 may be implanted under a flap of skin at the back of the neck. Neurostimulator 34 may be generally thin and flat and, in some embodiments, may be angled or curved to better conform to the curvature at the back of the patient's neck. In particular, neurostimulator 34 may have a degree of curvature selected to conform to a radius of the stimulation site. For example, the degree of curvature may be approximately 20 to 40 degrees, and more preferably approximately 30 degrees. With this radius of curvature, and a very thin housing, neurostimulator 34 exhibits a low profile and may be barely noticeable to patient 4 and others.

Neurostimulator 34 includes a battery, control circuitry, one or more electrodes to provide stimulation to the neuralgic region of patient 4, and wireless telemetry circuitry to communicate with an external programmer to permit adjustments to neurostimulation therapy or interrogation of the operational status of the neurostimulator. The battery within neurostimulator 34 may be rechargeable, and may have a capacity of at least 20 milliamp-hr. The control circuitry may include an application specific integrated circuit (ASIC) designed to minimize the number of components within the housing of neurostimulator 34. The electrodes may comprise an array of electrodes that provides the caregiver with enhanced programming flexibility. In particular, a caregiver may program neurostimulator 34, via wireless telemetry, to select particular electrodes for delivery of neurostimulation. In some cases, the array of electrodes may be integrated with the housing of neurostimulator 34 on a side adjacent the neuralgic region of patient 4. Various embodiments of neurostimulator 34 will be described in greater detail below.

Figure 8:
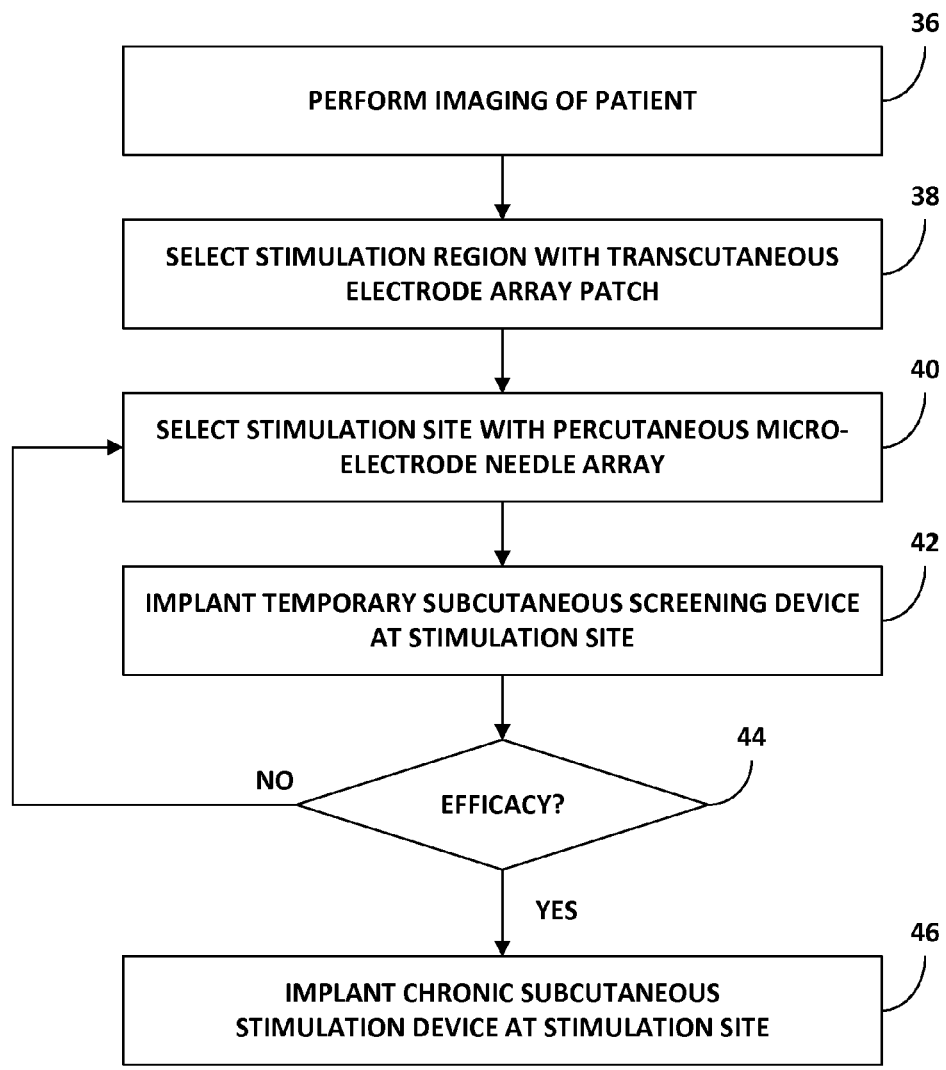
FIG. 8 is a flow chart illustrating a screening process to select a stimulation site for treatment of a neuralgic region of a patient.

FIG. 8 is a flow chart illustrating a multi-step screening process to select a stimulation site for treatment of the neuralgic region of patient 4. In general, the multi-step screening process may include a first step involving application of electrode array patch 6 for transcutaneous stimulation, a second step involving application of a micro-electrode needle array 20 for percutaneous stimulation, a third step involving temporary implantation of a subcutaneous trial stimulator 26, and a fourth step of chronic implantation of a subcutaneous stimulator 34. In the second step, the location of an efficacious stimulation region is further refined in order to select a stimulation site for temporary and chronic implantation. Although four steps are described, a lesser number of steps may be used in some embodiments. For example, one or more of the transcutaneous, percutaneous, or temporary subcutaneous steps may be omitted, although all of the steps may be desired in some embodiments.

As shown in FIG. 8, a caregiver, such as a physician or clinician, first may perform imaging, such as MRI, to identify epidermal region 8 of patient 4 adjacent the neuralgic region (36). Using the imaging results, the caregiver visualizes a target stimulation region. The caregiver then applies an electrode array patch 6 to the target stimulation region of patient 4, and activates screening controller 12 to apply transcutaneous stimulation. Based on feedback from the patient 4, the caregiver evaluates different electrode combinations to non-invasively select a first stimulation region that appears to provide relief for symptoms suffered by the patient (38). Screening controller 12 drives electrodes 10 on electrode array patch 6 to transcutaneously deliver neurostimulation energy in other stimulation regions.

Upon selection of a stimulation region, the caregiver applies micro-electrode needle array 20 in the vicinity of the stimulation region. In particular, the caregiver forces micro-electrode needle array 20 against the patient's neck so that needle electrodes 22 penetrate into tissue at the first stimulation region. The caregiver then uses screening controller 12 to apply stimulation via different combinations of percutaneous needle electrodes 22. By selecting different combinations of needle electrodes 22, and receiving feedback, the caregiver selects a stimulation site (40). The stimulation site is within the stimulation region defined by transcutaneous screening, and serves to further refine the location for delivery of stimulation. Screening controller 12 drives micro-electrode needle electrodes 22 on micro-electrode array 20 and may receive feedback from patient 4 regarding efficacy of stimulation. The caregiver selects the stimulation site within the stimulation region based on the feedback. In this way, the micro-electrode screening device further localizes the stimulation region for chronic implantation of neurostimulator 34.

Upon identification of the stimulation site, and prior to chronic implantation, the caregiver may subcutaneously implant a temporary implantable screening device 26 at the stimulation site to further evaluate the efficacy of the stimulation site (42). Temporary screening device 26 delivers stimulation energy subcutaneously. If the temporary screening device 26 is effective, the caregiver may then elect to chronically implant neurostimulator 34 at the stimulation site. If temporary implantable screening device 26 does not substantially alleviate pain at the neuralgic region (no branch of 44), however, the caregiver may select another stimulation site within the first stimulation region with the micro-electrode needle screening device (40). Temporary implantable screening device 26 is used to test the newly selected stimulation site for efficacy. If temporary implantable screening device 26 substantially alleviates pain at the neuralgic region (yes branch of 44), the physician chronically implants a subcutaneous neurostimulator 34 at the stimulation site (46).

Figure 9A:
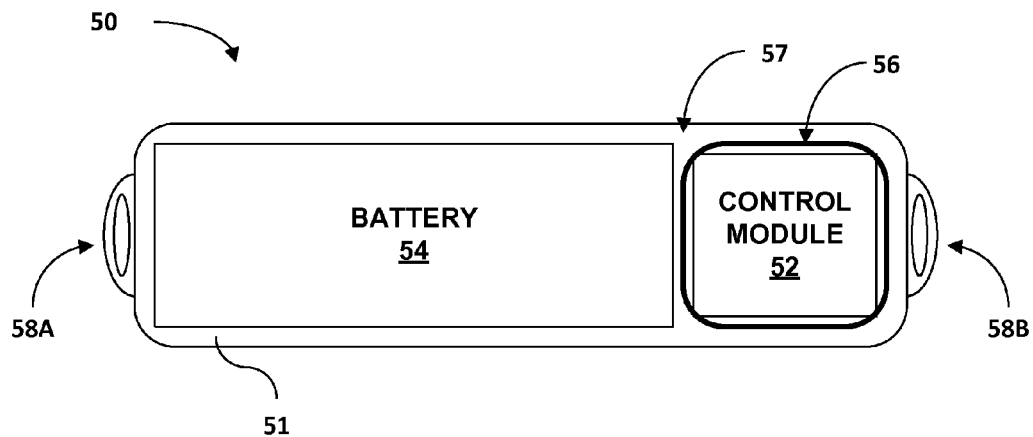
FIGS. 9A and 9B respectively illustrate a top view and a side view of a neurostimulator.

FIGS. 9A-18 illustrate various embodiments of a chronically implanted subcutaneous neurostimulator. Some of the structural and functional aspects depicted in FIGS. 9A-18 also may be used for a temporary subcutaneous neurostimulator. FIG. 9A illustrates a top view of a neurostimulator 50 for chronic subcutaneous implantation. FIG. 9B illustrates a side view of neurostimulator 50. Neurostimulator 50 is designed to deliver on-site neurostimulation for treatment of neuralgia experienced by a patient. Neurostimulator 50 may be subcutaneously implanted at a stimulation site adjacent a neuralgic region of the patient. For example, neurostimulator 50 may be subcutaneously implanted at the back of the neck of the patient to relieve occipital neuralgia, a migraine-like pain originating along the occipital nerve. As described above, a caregiver may select the stimulation site based on feedback from the patient to one or more of a transcutaneous stimulation screening device, a percutaneous micro-electrode needle array screening device, and a temporary subcutaneous implantable screening device.

Figure 9B:
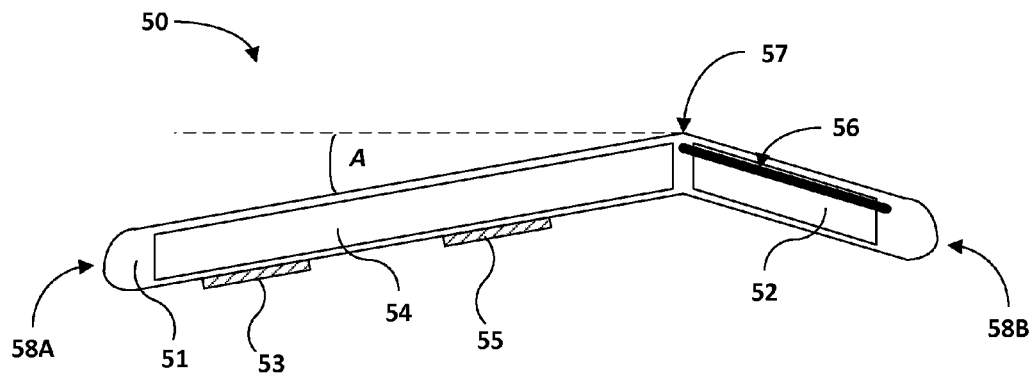

As shown in FIGS. 9A and 9B, neurostimulator 50 comprises a housing 51 that houses a control module 52, a battery 54, and a coil 56 encircling control module 52. Coil 56 may serve as an inductive power interface to recharge battery 54, as well as a telemetry coil for wireless communication with an external programmer. In some embodiments, coil 56 may encircle control module 52, battery 54, or both. Coil 56 inductively receives energy from an external recharging unit (not illustrated) through the skin of the patient to recharge battery 54. Coil 56 may be formed of windings of copper or another highly conductive material.

Neurostimulator 50 also includes two or more electrodes 53, 55 to provide stimulation to the neuralgic region of the patient. Control module 52 receives power from battery 54 to drive the electrodes 53, 55 according to a stimulation program included in control module 52. The electrodes 53, 55 may comprise a pair of electrodes or an array of electrodes, illustrated in FIGS. 10-12. An array of electrodes provides enhanced stimulation programming flexibility. In some cases, the array of electrodes may be integrated on housing 51 of neurostimulator 50, as shown in FIG. 9B.

As shown in FIG. 9A, housing 51 conforms to a substantially rectangular form factor. In this case, housing 51 may include the array of electrodes on a side of housing 51 positioned adjacent the neuralgic region. In other cases, the housing may conform to a substantially cylindrical form factor, illustrated in FIGS. 16-18, and include ring electrodes along a length of the housing.

Housing 51 may conform to a miniaturized form factor with a low profile in order to fit directly adjacent the neuralgic region of the patient. As illustrated in FIG. 9B, housing 51 may also comprise a degree of curvature to conform to a radius of the stimulation site. Housing 51 may be pre-formed with a degree of curvature. In other cases, the physician may bend housing 51 to a degree of curvature appropriate for a specific stimulation site. For example, housing 51 may comprise a flexible material or include bellows that allow housing 51 to bend. In either cases, housing 51 may be angled, curved or jointed to better accommodate the curvature at the back of the patient's neck.

In the example of FIGS. 9A and 9B, housing 51 has a joint 57 between the portion of the housing containing control module 52 and the portion containing battery 54. FIG. 9B, in particular, illustrates a desired radius of curvature that permits housing 51 to better conform to the geometry of the implant site at the back of the patient's neck. The radius of curvature may be expressed as an angle A defined between a line tangent to the apex of joint 57 and a line within either of the two major planes defined by housing 51, i.e., on either side of joint 57. As discussed previously, the angle A representing the desired radius of curvature may be approximately 20 to 40 degrees, and more preferably approximately 30 degrees.

Housing 51 may also define apertures 58A and 58B (collectively "apertures 58"). Apertures 58 may operate as both suture and removal holes. The physician may anchor neurostimulator 50 at the stimulation site adjacent the neuralgic region of the patient by suturing housing 51 to surrounding tissue via apertures 58. In order to remove neurostimulator 50 from the stimulation site, the physician may cut the sutures and then use a tool, e.g., a hook, that engages with at least one of apertures 58 to easily pull neurostimulator 50 out of the implantation site.

Battery 54 may comprise a rechargeable battery with a capacity of at least 20 milliamp-hr, more preferably at least 25 milliamp-hr, and still more preferably at least 30 milliamp-hours. In this case, battery 54 comprises a capacity almost an order of magnitude larger than conventional microstimulators. In some embodiments, battery 54 may comprise a lithium ion rechargeable battery. Control module 52 also couples to coil 56, which may operate as both a recharge coil and a telemetry coil. Control module 52 receives energy via recharge coil 56 to recharge battery 54. Control module 52 may also transmit or receive stimulation programming commands, instructions, or other instructions via telemetry coil 56.

Control module 52 may comprise an ASIC designed to minimize the number of components within neurostimulator 50. The ASIC may be designed with an IC using the 0.8 micron process in an effort to reduce the overall size and profile of neurostimulator 50. The ASIC may include both a battery recharge module and a telemetry module that couple to coil 56, as well as a pulse generator and processor. The processor directs the pulse generator to drive one or more electrodes based on stimulation programs stored in memory accessible by the control module 52 or received by the telemetry module. A power management module coupled to battery 54 powers the control circuitry within control module 52.

Housing 51 may be formed from any of a variety of materials such as silicone, polyurethane, other polymeric materials, titanium, stainless steel or ceramics. In some embodiments, as will be described, housing 51 may be generally soft and flexible, and may include a flexible member that at least partially encapsulates the battery 54, control module 52 and coil 56. In some embodiments, the flexible member may be an overmold that is molded about all or some of control module 52, battery 54 and coil 56. Control module 52 and coil 56 are designed to be very thin and flat to permit subcutaneous implantation. Similarly, battery 54 may be a lithium ion battery with a thin, generally flat housing or cylindrical housing. In the case of a pin type cell, battery 54 may have an aluminum housing with a crimped or riveted pin feedthrough. In some embodiments, battery 54 alternatively may comprise a foil pack battery. In an exemplary embodiment, neurostimulator 50 may have a length of approximately 30 to 50 mm, a width of approximately 10 to 20 mm and a thickness of approximately 3 to 6 mm.

Each of electrodes 53, 55 may be circular, square or rectangular. In the case of a circular shape, each electrode, may have a diameter of approximately 0.5 to 1.5 mm, and more preferably 1 mm. Although two electrodes 53, 55 are shown in FIGS. 9A and 9B, a larger number of electrodes may be provided in a linear or two-dimensional array. For example, neurostimulator 50 may include between approximately 2 and 32 electrodes, distributed in a linear or two-dimensional array. A linear array generally refers to an ordering of electrodes along a common line, whereas a two-dimensional array generally refers to an ordering of electrodes along at least two different lines, e.g., as rows and columns. In either case, the array of electrodes may have a regular, periodic pattern such that electrodes are positioned at regular spatial intervals within a line, row or column. Alternatively, the array may be irregular such that electrodes are positioned at irregular intervals or at positions that do not represented an ordered pattern.

Figure 10:
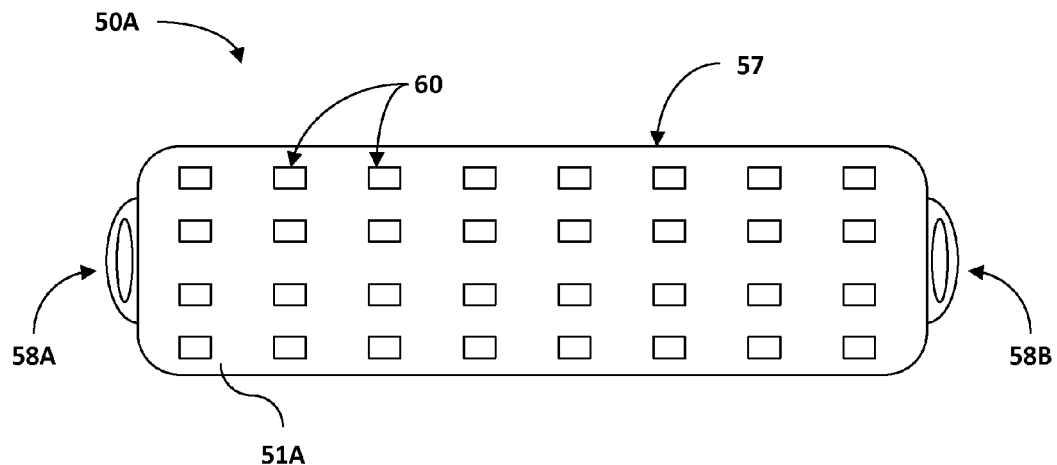
FIG. 10 is a schematic diagram illustrating an exemplary bottom view of a neurostimulator in accordance with an embodiment of the invention.
Figure 11:
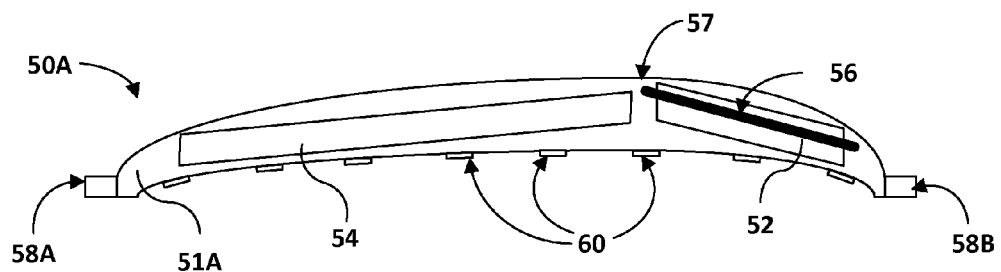
FIG. 11 is an exemplary side view of the neurostimulator of FIG. 10.

FIG. 10 is a schematic diagram illustrating a bottom view of a neurostimulator 50A in accordance with an alternative embodiment of the invention. FIG. 11 is an exemplary side view of the neurostimulator of FIG. 10. Neurostimulator 50A comprises a housing 51A and apertures 58. Neurostimulator 50A may be substantially similar to neurostimulator 50 of FIGS. 9A and 9B. However, neurostimulator 50A includes a two-dimensional array of electrodes 60 integrated on housing 51A. In other embodiments, a linear array of electrodes 60 may be provided.

Each of electrodes 60 may be coupled to control module 52 within housing 51A. A combination of electrodes 60, such as a bipolar electrode pair, may be selected based on the position of the electrodes relative the stimulation site identified in the screening process. For example, neurostimulator 50 may be initially programmed to deliver stimulation energy via a combination of electrodes that are positioned closest to the identified stimulation site. Alternatively, a unipolar arrangement may be selected.

Neurostimulator 50A may have a joint 57, as in FIGS. 8 and 9, between the portion of the housing containing a control module and the portion containing a battery, thereby promoting conformance to the back of the neck of a patient. The caregiver may implant neurostimulator 50A at the selected stimulation site with the array of electrodes 60 directly adjacent the neuralgic region of the patient. The array of electrodes 60 allows the caregiver flexibility in programming the stimulation pattern provided by neurostimulator 50A.

Like housing 51 in FIGS. 9A and 9B, housing 51A of FIG. 10 may have a substantially miniaturized form factor and a low profile to fit within the stimulation site. A control module within neurostimulator 50A can be programmed to apply selected combinations of the electrodes 60 to achieve desired efficacy. In particular, at the time of implantation, a caregiver may test different electrode combinations and program neurostimulator 50A to apply a selected combination. Again, the programming may take place by wireless telemetry via a coil carried by neurostimulator 50A.

Figure 12:
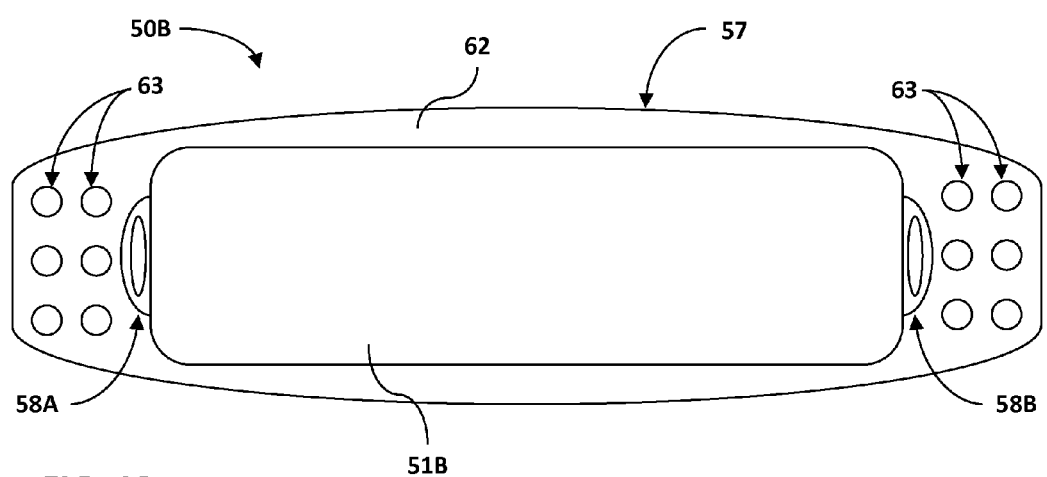
FIG. 12 is a schematic diagram illustrating another exemplary bottom view of a neurostimulator in accordance with another embodiment of the invention.

FIG. 12 is a schematic diagram illustrating another exemplary bottom view of a neurostimulator 50B in accordance with an embodiment of the invention. Neurostimulator 50B comprises a housing 51B and apertures 58. Neurostimulator 50B may be substantially similar to neurostimulator 50 from FIGS. 9A and 9B. However, neurostimulator 50B includes a flexible member 62, such as an overmold, that encapsulates housing 51B. In some cases, flexible member 62 may only partially encapsulate housing 51B. Neurostimulator 50B also includes an array of electrodes 63 integrated on flexible member 62 at opposing ends of housing 51B. Each of electrodes 63 may couple to control module 52 within housing 51B. At least a portion of each electrode 63 protrudes through flexible member 62 for contact with tissue within patient 4.

The physician may implant neurostimulator 50B at the selected stimulation site with the array of electrodes 63 adjacent the neuralgic region of the patient. Flexible member 62 may comprise a substantially flexible polymer with tapered edges. In this way, flexible member 62 allows more flexibility in the placement of electrodes 63 than integrating the electrodes into the housing, as illustrated in FIG. 10. Furthermore, flexible member 62 may smooth the transition from housing 51B to the tissue surrounding neurostimulator 50B. Although neurostimulator 50B has a larger volume than a neurostimulator without a flexible member, e.g., neurostimulator 50A, flexible member 62 may improve cosmesis and prevent erosion of the epidermal region adjacent the stimulation site.

Figure 13:
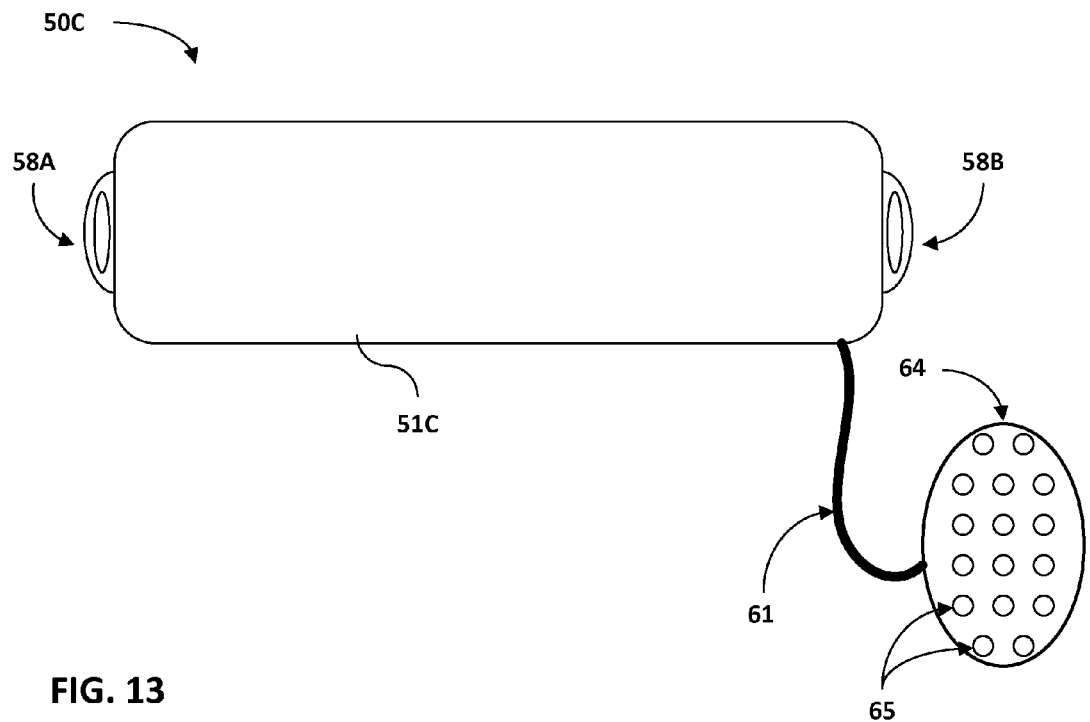
FIG. 13 is a schematic diagram illustrating another exemplary bottom view of a neurostimulator in accordance with an embodiment of the invention.

FIG. 13 is a schematic diagram illustrating another exemplary bottom view of a neurostimulator 50C in accordance with an embodiment of the invention. Neurostimulator 50C comprises a housing 51C and apertures 58. Neurostimulator 50C is substantially similar to neurostimulator 50 from FIGS. 9A and 9B. However, neurostimulator 50C further includes an electrode array 64 tethered to housing 51C, via a cable 61. Electrode array 64 includes an array of electrodes 65. In some cases, electrode array 64 comprises a flexible polymer and electrodes 65 may be potted in electrode array 64. Each of electrodes 65 may couple to control module 52 within housing 51C via conductors within cable 61.

The physician may implant neurostimulator 50C at the selected stimulation site with the tethered array of electrodes 65 adjacent the neuralgic region of the patient. Tethered electrode array 64 allows more flexibility in the placement of electrodes 64. However, neurostimulator 50C may have a larger overall implantation volume than a neurostimulator with electrodes integrated on a housing, e.g., neurostimulator 50A, or on a flexible member, e.g., neurostimulator 50B.

In some cases, electrode array 64 may comprise a thinner profile than neurostimulator 50C such that electrode array 64 may be positioned directly at the stimulation site and neurostimulator 50C may be positioned near the stimulation site at a more desirable implantation site. In this way, neurostimulator 50C may improve cosmesis and prevent erosion of the epidermal region adjacent the stimulation site.

Figure 14:
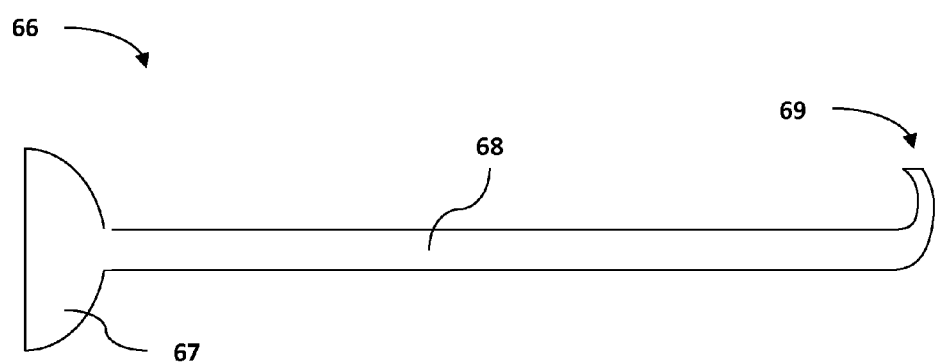
FIG. 14 is a schematic diagram illustrating an exemplary tool for insertion or removal of a neurostimulator.

FIG. 14 is a schematic diagram illustrating an exemplary tool 66 for insertion or removal of a neurostimulator. The physician may use tool 66 when implanting or explanting neurostimulator 50 from FIGS. 9A and 9B. Tool 66 comprises a base 67, a shaft 68, and a hook 69. The physician may subcutaneously implant neurostimulator 50 by engaging hook 69 with one of apertures 58 of neurostimulator 50 and feeding neurostimulator 50 into the stimulation site with shaft 68. The physician may grip base 67 to manipulate neurostimulator 50 into the proper position. The physician may explant neurostimulator 50 from the stimulation site by subcutaneously inserting shaft 68 at the stimulation site and engaging hook 69 with one of apertures 58 of neurostimulator 50. The physician then grips base 67 and pulls neurostimulator 50 out of the stimulation site. In some cases, shaft 68 may comprise an adjustable length to allow the physician to reach a variety of stimulation sites without requiring different tools.

Figure 15A:
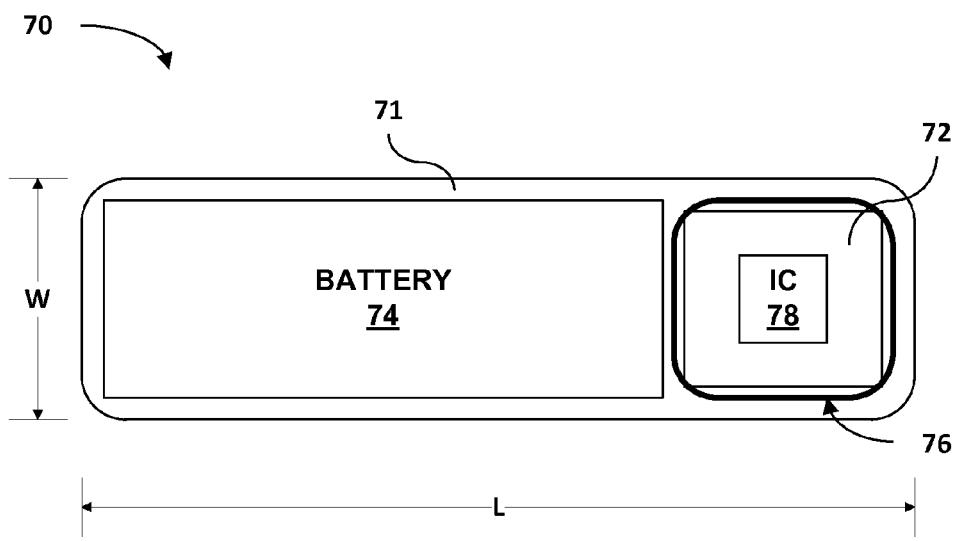
FIGS. 15A and 15B respectively illustrate a top view and a side view of a neurostimulator.
Figure 15B:
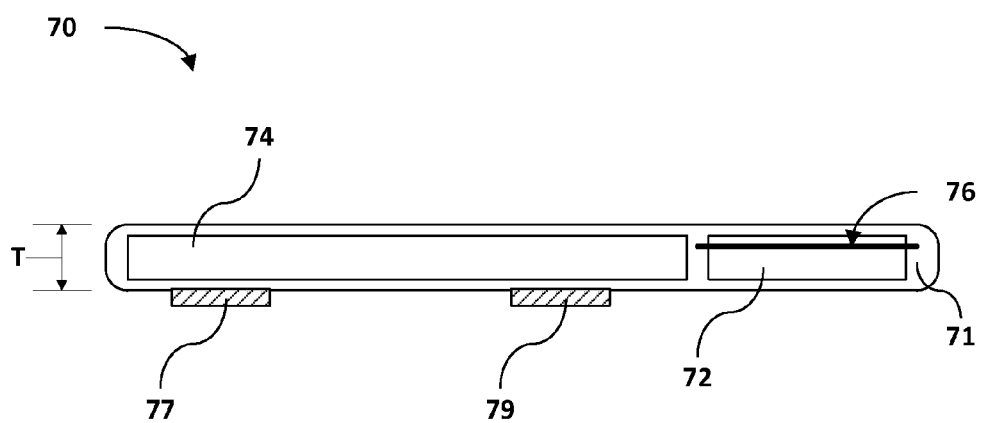

FIG. 15A illustrates a top view of another neurostimulator 70. FIG. 15B illustrates a side view of neurostimulator 70. Neurostimulator 70 may be substantially similar to neurostimulator 50 from FIGS. 9A and 9B. For example, neurostimulator 70 may be subcutaneously implanted at a stimulation site adjacent a neuralgic region of a patient. In particular, neurostimulator 70 may be subcutaneously implanted at the back of the neck of the patient to relieve occipital neuralgia. However, housing 71 may have a substantially rectangular form factor.

As shown in FIGS. 15A and 15B, neurostimulator 70 comprises a housing 71 that houses a control module 72, a battery 74, and a coil 76 encircling control module 72. Neurostimulator 70 also includes two or more electrodes 77, 79 to provide stimulation to the neuralgic region of the patient. Control module 72 receives power from battery 74 to drive the electrodes according to a stimulation program included in control module 72. The electrodes 77, 79 alternatively may comprise a linear or two-dimensional array of electrodes substantially similar to the examples of neurostimulator 50 illustrated in FIGS. 10-13.

Housing 71 conforms to a substantially rectangular form factor. In this case, housing 71 may include the array of electrodes integrated on a side of housing 71 positioned adjacent the neuralgic region. Housing 71 conforms to a miniaturized form factor with a low profile in order to fit directly adjacent the neuralgic region of the patient. For example, housing 71 may have a length L less than approximately 50 mm, a width of less than approximately 20 mm, and a thickness of less than approximately 6 mm. In a specific example for the housing 71 illustrated in FIGS. 15A and 15B, housing 71 comprises a length L of less than or equal to 36.6 mm (1.44 inches), and width W of less than or equal to 14.5 mm (0.57 inches), and a thickness T of less than or equal to 4.5 mm (0.177 inches). In some embodiments, housing 71 may include approximately 0.25 mm (0.01 inches) of insulation between control module 72 and battery 74 and housing 71. The walls of housing 71 may comprise a total thickness of approximately 0.71 mm (0.03 inches).

Battery 74 may comprise a rechargeable battery with a capacity of at least 20 milliamp-hours, more preferably at least 25 milliamp-hours, and still more preferably at least 30 milliamp-hours. In some embodiments, battery 74 may comprise a lithium ion rechargeable battery. Battery 74 may conform to a miniaturized form factor to fit within housing 71. Battery 74 may comprise a length of less than or equal to approximately 24.9 mm (0.98 inches), a width of less than or equal to approximately 12.7 mm (0.50 inches), and a thickness of less than or equal to approximately 3.3 mm (0.13 inches). Battery 74 may conform to one of a variety of designs. Some examples are given in Table 1 below.

TABLE 1

|  | 3.0 mm thick standard loading | 3.0 mm thick adjustable loading | 3.3 mm thick standard loading | 3.3 mm thick adjustable loading |
| --- | --- | --- | --- | --- |
| Length (mm) | 25.4 | 25.4 | 25.4 | 24.9 |
| Width (mm) | 16.5 | 14.2 | 13.2 | 12.7 |
| Capacity (mA-hr) | 30 | 30 | 31 | 30 |
| Case volume (cc) | 1.26 | 1.08 | 1.11 | 1.04 |
| Coating (mg/cm$^2$) | 22 | 12.1 | 22 | 12.32 |

Neurostimulator 70 may be over-discharge protected. However, since battery 74 conforms to an extremely small form factor, the over-discharge protection may be difficult to realize using traditional approaches, such as extra battery capacity. Therefore, neurostimulator 70 may include a switch to disconnect battery 74 from the load when a predetermined voltage is reached. In other cases, battery 74 may comprise an over-discharge tolerant battery.

Control module 72 may also conform to a miniaturized form factor to fit within housing 71. Control module 72 may comprise a length of less than or equal to approximately 6.5 mm (0.256 inches), a width of less than or equal to approximately 9.4 mm (0.37 inches), and a thickness of less than or equal to approximately 3.6 mm (0.14 mm). Control module 72 also couples to coil 76 that may operate as both a recharge coil and a telemetry coil. Control module 72 may receive energy via recharge coil 76 to recharge battery 74. Control module 72 may also receive stimulation programs and other instructions from the patient, the physician, or the clinician via telemetry coil 76.

Although battery 74 comprises a capacity almost an order of magnitude larger than some conventional microstimulators, battery 74 has a relatively small capacity compared to full size neurostimulators. Therefore, coil 76 may comprise a smaller coil than traditional neurostimulators. Coil 76 comprises inner dimensions slightly larger than the dimensions of control module 72 given above. Coil 76 may comprise an inner length of approximately 6.7 mm (0.265 inches) and an inner width of approximately 9.7 mm (0.38 inches). The outer dimensions of coil 76 may comprise an outer length of approximately 8.4 mm (0.33 inches) and an outer width of approximately 11.7 mm (0.46 inches). Coil 76 may also comprise a thickness of approximately 2.5 mm (0.10 inches).

Control module 72 comprises an application specific IC 78 designed to minimize the number of components within neurostimulator 70. IC 78 may be designed using the 0.8 micron process in an effort to reduce the overall size and profile of neurostimulator 70. With sufficient processing power, IC 78 may have a footprint of approximately 5.2 mm (0.204 inches) by 5.2 mm and a thickness of approximately 0.46 mm (0.018 inches).

Figure 16:
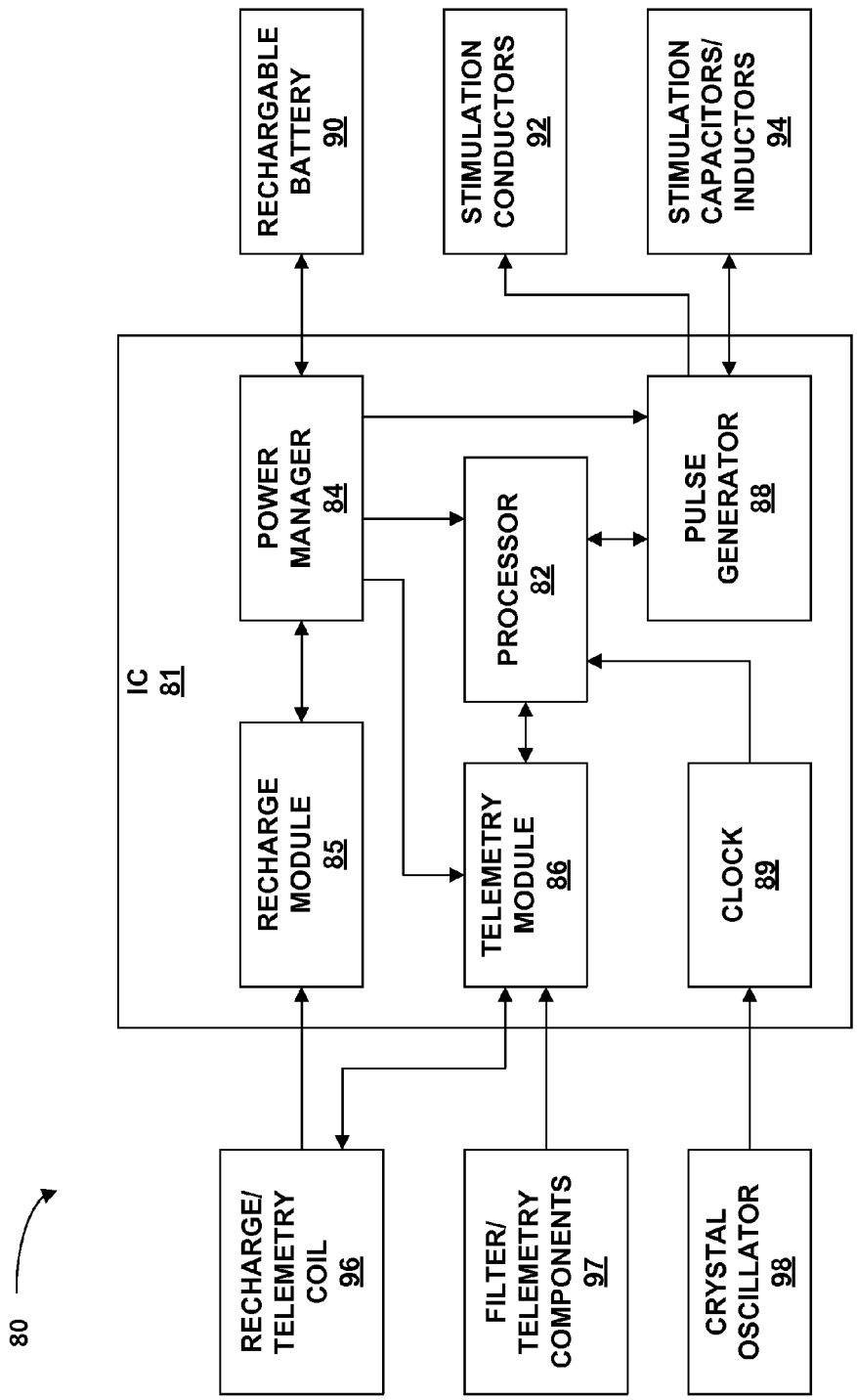
FIG. 16 is a block diagram illustrating an exemplary control module included in an on-site neurostimulator for the treatment of neuralgia experienced by a patient.

FIG. 16 is a block diagram illustrating an exemplary control module 80 included in an on-site neurostimulator for the treatment of neuralgia experienced by a patient. Control module 80 may be used to form control module 72 of neurostimulator 70 illustrated in FIGS. 15A and 15B or control module 52 illustrated in FIGS. 9A and 9B. Control module 80 comprises an IC 81, stimulation capacitors and inductors 94, filter and telemetry components 97, and a crystal oscillator 98 positioned on a substrate board. The substrate board may comprise a minimal number of layers, e.g. four layers or less, and comprise a thickness equal to or less than approximately 0.4 mm (0.014 inches).

Control module 80 couples to a rechargeable battery 90, conductors 92 that connect to one or more stimulation electrodes of the neurostimulator, and a recharge and telemetry coil 96. Rechargeable battery 90 may have a capacity of at least 20 milliamp-hours, more preferably at least 25 milliamp-hours, and still more preferably at least 30 milliamp-hours. In some embodiments, battery 90 may comprise a lithium ion rechargeable battery. Coil 96 operates as both a recharge coil and a telemetry coil. In some cases, as described above, coil 96 may encircle control module 80.

IC 81 may be formed as an ASIC designed to minimize the number of components within the neurostimulator. IC 81 may be designed using the 0.8 micron process in an effort to reduce the overall size and profile of the neurostimulator. IC 81 may operate substantially similar to IC 78 of control module 72 (FIG. 15A). IC 81 includes a processor 82, a power manager 84, a recharge module 85, a telemetry module 86, a pulse generator 88, and a clock 89.

Power manager 84 couples to rechargeable battery 90 to provide power to processor 82, recharge module 85, telemetry module 86, and pulse generator 88. Recharge module 85 couples to recharge and telemetry coil 96 and receives power via coil 96 to recharge battery 90. Telemetry module 86 also couples to recharge and telemetry coil 96 and receives stimulation programs and other instructions from a programmer operated by the patient or physician via coil 96. Filter, power management, telemetry components 97 couple to telemetry module 86 to support reliable wireless communication. Examples of filter, power management and telemetry components 97 include a telemetry tank capacitor, voltage regulation filters, power supply filters, and battery bypass capacitors. Telemetry module 86 then provides the received stimulation programs to processor 82, which stores the programs in memory (not shown).

Crystal oscillator 98 is coupled to clock 89, which clocks processor 82 to run the stimulation programs. Processor 82 directs pulse generator 88 to provide stimulation to the electrodes of the neurostimulator via stimulation conductors 92. Processor 82 directs pulse generator 88 according to the stimulation programs received from telemetry module 86 and the clock cycle received from clock 89. Pulse generator 88 is coupled to stimulation capacitors and inductors 94, which include capacitors to store stimulation pulses.

Figure 17:
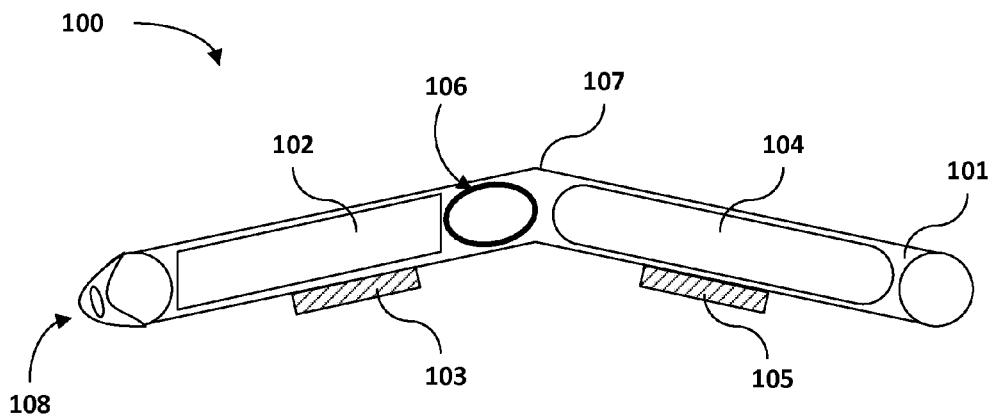
FIG. 17 illustrates a neurostimulator that provides on-site treatment of neuralgia experienced by a patient.

FIG. 17 illustrates another neurostimulator 100 that provides on-site treatment of neuralgia experienced by a patient. Neurostimulator 100 may substantially conform to the neurostimulators shown in FIGS. 9A-16. For example, neurostimulator 100 can be subcutaneously implanted at a stimulation site adjacent a neuralgic region of the patient. Neurostimulator 100 comprises a housing 101 that houses a control module 102, a battery 104, and a coil 106.

Neurostimulator 100 also includes two or more electrodes 103, 105 to provide stimulation to the neuralgic region of the patient. Control module 102 receives power from battery 104 to drive the electrodes 103, 105 according to a stimulation program included in control module 102. The electrodes 103, 105 may alternatively include an array of electrodes that provides enhanced stimulation programming flexibility. The array of electrodes may be integrated on housing 101 of neurostimulator 100.

Housing 101 conforms to a substantially cylindrical form factor and may include ring electrodes along a length of housing 101. Housing 101 may conform to a miniaturized form factor with a small diameter in order to fit directly adjacent the neuralgic region of the patient. Housing 101 may also comprise a degree of curvature to conform to a radius of the stimulation site.

Housing 101 may be pre-formed with a degree of curvature. As illustrated in FIG. 17, housing 101 has a joint 107. In some embodiments, housing 101 may permit the physician to bend the housing to a degree of curvature appropriate for a specific stimulation site. For example, housing 101 may comprise a flexible material or include bellows, illustrated in FIGS. 19 and 20, that allow housing 101 to bend.

In some embodiments, housing 101 may also define a hole 108 that operates in conjunction with either an insertion hook for implantation or removal hook for explantation. The physician may insert neurostimulator 100 at the stimulation site adjacent the neuralgic region of the patient by engaging a tool with hook 108 and feeding neurostimulator 100 into the stimulation site. In order to remove neurostimulator 100 from the stimulation site, the physician may again use the tool to engage hole 108 and pull neurostimulator 100 out of the patient.

Figure 18:
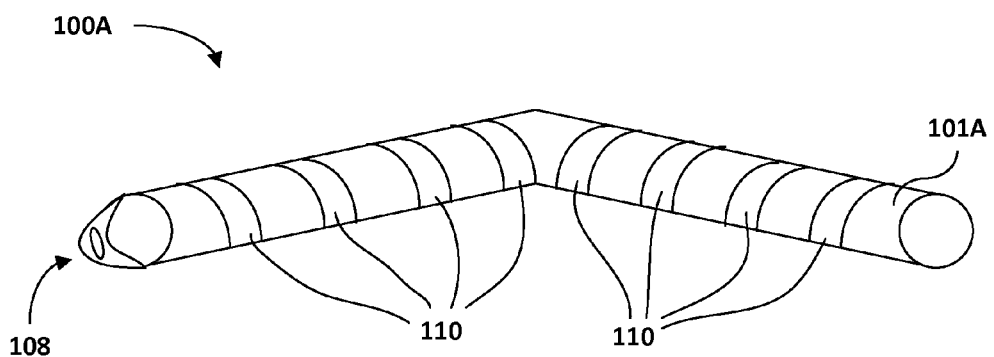
FIG. 18 is a schematic diagram illustrating an exemplary external view of a neurostimulator in accordance with an embodiment of the invention.

As in the examples of FIGS. 9A-15, battery 104 of neurostimulator 100 may comprise a rechargeable battery with a capacity of at least 20 milliamp-hours, more preferably at least 25 milliamp-hours, and still more preferably at least 30 milliamp-hours. Control module 102 is coupled to coil 106, which operates as both a recharge coil and a telemetry coil FIG. 18 is a schematic diagram illustrating a neurostimulator 101A in accordance with an embodiment of the invention. Neurostimulator 100A comprises a housing 101A, which defines a hole 108. Neurostimulator 100A is substantially similar to neurostimulator 100 from FIG. 18. Neurostimulator 100A includes an array of ring electrodes 110 integrated along housing 101A. Ring electrodes 110 may extend entirely or partially around a circumference of housing 101A. Each of electrodes 110 is coupled to control module 102 within housing 101A. The physician may implant neurostimulator 100A at the selected stimulation site with the array of electrodes 110 directly adjacent the neuralgic region of the patient. The array of electrodes 110 allows the physician or clinician flexibility in programming the stimulation provided by neurostimulator 100

Figure 19:
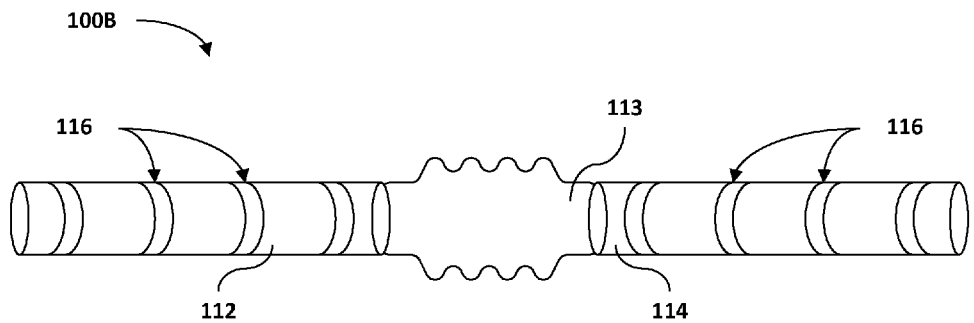
FIG. 19 is a schematic diagram illustrating another exemplary external view of a neurostimulator in accordance with an embodiment of the invention.

FIG. 19 is a schematic diagram illustrating a neurostimulator 101B in accordance with another embodiment of the invention. Neurostimulator 100B is substantially similar to neurostimulator 100 of FIG. 17. Neurostimulator 100B comprises a first housing portion 112 and a second housing portion 114. First and second housing portions 112 and 114 are connected by a bellows-like joint 113. Neurostimulator 100B includes an array of ring electrodes 116 integrated along first housing portion 112 and second housing portion 114. First and second housing portions 114 may be formed from a variety of materials such as titanium, stainless steel, ceramic material, silicone, polyurethane or other polymeric materials.

Each of electrodes 116 is coupled to control module 102 within neurostimulator 100B. The physician may implant neurostimulator 100B at the selected stimulation site with the array of electrodes 116 directly adjacent the neuralgic region of the patient. First and second housing portions 112 and 114 may conform to a substantially miniaturized form factor and a small diameter to fit within the stimulation site. For example, the stimulation site may be located in the back of the neck of the patient for neurostimulator 100B to treat occipital neuralgia.

Figure 20:
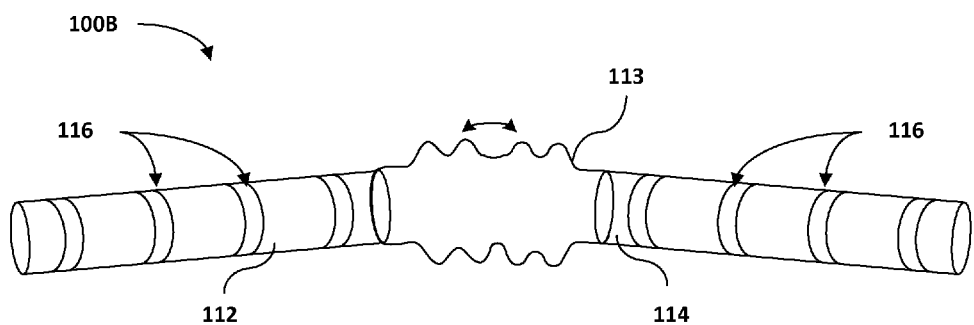
FIG. 20 is a schematic diagram illustrating the neurostimulator of FIG. 19 in a slightly bent position to better conform to an implantation site.

As illustrated in FIG. 19, neurostimulator 100B includes bellows-like joint 113 that allows bending of neurostimulator 100B. FIG. 20 is a schematic diagram illustrating neurostimulator 100B in a slightly bent position to better conform to an implantation site. For example, the physician may bend neurostimulator 100B about bellows-like joint 113 to a degree of curvature that conforms to a radius of the specific stimulation site. Bellows-like joint 113 may comprise titanium, nitinol, or another biocompatible material strong enough to withstand flexing. Bellows-like joint 113 may be substantially smaller relative to neurostimulator 100B if the material of bellows 113 is able to withstand the increased flexing force.

Various embodiments of the invention have been described. The foregoing description of the exemplary embodiments of the invention has been presented for the purposes of illustration and description. They are not intended to be exhaustive or to limit the invention to the precise forms disclosed. Many modifications and variations are possible in light of the above teaching.

For example, although application of various embodiments of the invention to occipital neuralgia has been described for purposes of illustration, the invention may be applied to treat a variety of disorders. It is intended that the scope of the invention be limited not with this detailed description, but rather by the claims. These and other embodiments are within the scope of the following claims.

The invention claimed is:

1. An implantable neurostimulator device comprising:
a pulse generator that generates neurostimulation pulses configured to treat occipital neuralgia;
a set of electrodes, coupled to the pulse generator, that delivers the neurostimulation pulses; and
a device housing that houses the pulse generator, wherein the device housing is sized and curved to fit within and to at least partially conform to a subcutaneous region within a back of a neck of a patient when the device housing is implanted in the subcutaneous region, and wherein the electrodes are arranged in a two-dimensional array on a surface of the housing.

2. The device of claim 1, wherein the device housing comprises a first side and a second side, wherein the electrodes are formed on the second side of the device housing for placement adjacent a neuralgic region within the back of the neck of the patient.

3. The device of claim 1, wherein the device housing has a thickness substantially smaller than a width of the device housing.

4. The device of claim 1, further comprising a flexible member that at least partially encapsulates the device housing.

5. The device of claim 4, wherein at least one electrode of the set of electrodes protrudes through the flexible member.

6. The device of claim 1, wherein the device housing is bendable to at least partially conform to the subcutaneous region within the back of the neck of the patient.

7. The device of claim 1, wherein the housing comprises a degree of curvature to conform to a radius of a stimulation site in the subcutaneous region within the back of the neck of the patient.

8. The device of claim 1, wherein the device housing defines one or more holes to receive a suture to anchor the housing at the stimulation site.

9. The device of claim 1, further comprising:
a rechargeable battery within the device housing; and
an inductive coil to receive energy from an external power source to recharge the battery.

10. The device of claim 1, further comprising a telemetry coil to support communication with an external device.

11. The device of claim 1, wherein the device housing has a thickness of less than or equal to approximately 4.5 millimeters.

12. The device of claim 1, wherein the device housing has a length of less than or equal to approximately 50 millimeters, a width of less than or equal to approximately 20 millimeters, and a thickness of less than or equal to approximately 6 millimeters.

13. The device of claim 1, wherein the two-dimensional array comprises one of an array of electrodes arranged in rows and columns of electrodes or an array of electrodes arranged in a recurring diagonal pattern of electrodes.

14. An implantable neurostimulator device comprising:
a neurostimulation generator that generates neurostimulation configured to treat occipital neuralgia;
a set of electrodes, coupled to the neurostimulation generator, that delivers the neurostimulation;
a device housing that houses the neurostimulation generator, wherein the device housing is sized and curved to fit within and at least partially conform to a subcutaneous region within a back of a neck of a patient when the device housing is implanted in the subcutaneous region; and
a flexible member that at least partially encapsulates the device housing, wherein at least one electrode of the set of electrodes protrudes through the flexible member.

15. The device of claim 14, wherein the electrodes are arranged in a two-dimensional array on a surface of the device housing.

16. The device of claim 14, wherein the housing comprises a first side and a second side, and wherein the electrodes are formed on the second side of the housing for placement adjacent a neuralgic region within the back of the neck of the patient.

17. The device of claim 14, wherein the device housing is bendable to at least partially conform to the subcutaneous region within the back of the neck of the patient.

18. The device of claim 14, wherein the device housing comprises a degree of curvature to at least partially conform to a radius of a stimulation site in the subcutaneous region within the back of the neck of the patient.

19. The device of claim 14, wherein the device housing defines one or more holes to receive a suture to anchor the device housing at the stimulation site.

20. The device of claim 14, wherein the device housing has a thickness of less than or equal to approximately 4.5 millimeters.

21. The device of claim 14, wherein the device housing has a length of less than or equal to approximately 50 millimeters, a width of less than or equal to approximately 20 millimeters, and a thickness of less than or equal to approximately 6 millimeters.

22. The device of claim 21, wherein the two-dimensional array comprises one of an array of electrodes arranged in rows and columns of electrodes or an array of electrodes arranged in a recurring diagonal pattern of electrodes.

23. The device of claim 14, further comprising:
a rechargeable battery within the device housing; and
an inductive coil to receive energy from an external power source to recharge the battery.

24. An implantable neurostimulator device comprising:
a neurostimulation generator that generates neurostimulation configured to treat occipital neuralgia;
a set of electrodes, coupled to the neurostimulation generator, that delivers the neurostimulation; and
a device housing that houses the neurostimulation generator, wherein the device housing is sized to fit within and at least partially conform to a subcutaneous region within a back of a neck of a patient when the device housing is implanted in the subcutaneous region,
wherein the electrodes are arranged in a two-dimensional array on a surface of the device housing.

25. The device of claim 23, wherein the two-dimensional array comprises one of an array of electrodes arranged in rows and columns of electrodes or an array of electrodes arranged in a recurring diagonal pattern of electrodes.

26. The device of claim 23, wherein the device housing is curved to at least partially conform to a radius of a stimulation site in the subcutaneous region within the back of the neck of the patient.

27. The device of claim 23, wherein the device housing comprises a first side and a second side, and wherein the electrodes are formed on the second side of the device housing for placement adjacent a neuralgic region within the back of the neck of the patient.

28. The device of claim 23, further comprising a flexible member that at least partially encapsulates the device housing, and wherein at least one electrode of the set of electrodes protrudes through the flexible member.

29. The device of claim 23, wherein the device housing is bendable to at least partially conform to the subcutaneous region within the back of the neck of the patient.

30. The device of claim 23, wherein the device housing comprises a degree of curvature to conform to a radius of a stimulation site in the subcutaneous region within the back of the neck of the patient.

31. The device of claim 23, further comprising:
a rechargeable battery within the device housing; and
an inductive coil to receive energy from an external power source to recharge the battery.

32. A device comprising:
a pulse generator that generates neurostimulation pulses configured to treat occipital neuralgia;
a set of electrodes, coupled to the pulse generator, that delivers the neurostimulation pulses;
a device housing that houses the pulse generator, wherein the device housing is sized and curved to fit within and at least partially conform to a subcutaneous region within a back of a neck of a patient when the device housing is implanted in the subcutaneous region; and
a flexible member that at least partially encapsulates the device housing, wherein at least one electrode of the set of electrodes protrudes through the flexible member.

33. The device of claim 31, wherein the electrodes are arranged in a two-dimensional array on a surface of the device housing.

34. The device of claim 31, wherein the two-dimensional array comprises one of an array of electrodes arranged in rows and columns of electrodes or an array of electrodes arranged in a recurring diagonal pattern of electrodes.

35. The device of claim 31, wherein the device housing comprises a first side and a second side, and wherein the electrodes are formed on the second side of the device housing for placement adjacent a neuralgic region within the back of the neck of the patient.

36. The device of claim 31, wherein the device housing is bendable to at least partially conform to the subcutaneous region within the back of the neck of the patient.

37. The device of claim 31, wherein the device housing comprises a degree of curvature to at least partially conform to a radius of a stimulation site in the subcutaneous region within the back of the neck of the patient.

38. The device of claim 31, further comprising:
a rechargeable battery within the device housing; and
an inductive coil to receive energy from an external power source to recharge the battery.

* * * * *